(12) United States Patent
Kawarai

(10) Patent No.: US 11,452,882 B2
(45) Date of Patent: Sep. 27, 2022

(54) MAGNETIC FIELD GENERATING-APPARATUS FOR BIOSTIMULATION

(71) Applicant: SUMIDA CORPORATION, Tokyo (JP)

(72) Inventor: Mitsugu Kawarai, Natori (JP)

(73) Assignee: SUMIDA CORPORATION, Tokyo (JP)

( * ) Notice: Subject to any disclaimer, the term of this patent is extended or adjusted under 35 U.S.C. 154(b) by 441 days.

(21) Appl. No.: 16/589,450

(22) Filed: Oct. 1, 2019

(65) Prior Publication Data

US 2020/0108265 A1    Apr. 9, 2020

(30) Foreign Application Priority Data

Oct. 9, 2018  (JP) .............................. JP2018-191206

(51) Int. Cl.
*A61N 2/02*    (2006.01)
(52) U.S. Cl.
CPC ..................................... *A61N 2/02* (2013.01)
(58) Field of Classification Search
CPC .................................. A61N 2/02; A61N 2/06
See application file for complete search history.

(56) References Cited

U.S. PATENT DOCUMENTS

| 2012/0029264 | A1* | 2/2012 | Roth | A61N 2/02 |
| | | | | 600/14 |
| 2018/0071544 | A1* | 3/2018 | Ghiron | A61N 2/02 |
| 2018/0169429 | A1* | 6/2018 | Zrenner | A61N 2/006 |

FOREIGN PATENT DOCUMENTS

| DE | 2707574 A1 | 8/1978 |
| JP | 08052231 A | 2/1996 |
| JP | 2005237681 A | 9/2005 |
| JP | 2009226037 A | 10/2009 |

OTHER PUBLICATIONS

EPO Extended European Search Report for corresponding EP Application No. 19201847.1, dated Mar. 13, 2020.

* cited by examiner

*Primary Examiner* — Christine H Matthews
(74) *Attorney, Agent, or Firm* — Cantor Colburn LLP

(57) ABSTRACT

A magnetic field generating-apparatus for biostimulation including: a core formed by magnetic material; and coils wound around portions of the cores, wherein the core includes at least two pairs of leg portions which are juxtaposed each other, in which for the respective two pairs of leg portions, there are provided gap-portions which mutually cross each other, the coils include first coil portions and second coil portions forming a first magnetic-path and a second magnetic-path between the two pairs of leg portions and the gap-portions respectively; and wherein there is generated a magnetic field of first direction which lies on the first magnetic-path, there is generated a magnetic field of second direction which lies on the second magnetic-path, and depending on a magnetic field formed by synthesizing the magnetic field of first direction and the magnetic field of second direction, a living body is stimulated.

19 Claims, 19 Drawing Sheets

MAGNETIC FIELD GENERATING-APPARATUS FOR BIOSTIMULATION

CROSS REFERENCES TO RELATED APPLICATIONS

The present invention contains subject manner related to Japanese Patent Application JP2018-191206 filed in the Japanese Patent Office on Oct. 9, 2018, the entire contents of which being incorporated herein by reference.

BACKGROUND OF THE INVENTION

Field of the Invention

The present invention relates to a magnetic field generating-apparatus for biostimulation.

Description of the Related Art

As medical-use rehabilitation equipment used for such as dementia improvement or the like, there goes into circulation an AC magnetic field generating-apparatus which applies strong magnetic field to the inside of a living body.

For such a magnetic field generating-apparatus, electricity is charged into a capacitor and is discharged through a switch unit to a serially connected coil, in which by flowing an impulse-shaped electric current through the coil with an LC resonance frequency, there is generated an AC magnetic field. Then, there has been requested an apparatus which can operate stably and continuously even in a case in which a joule heat is generated when flowing an electric current through the coil.

For example, in a Patent Document 1 (Japanese unexamined patent publication No. H8-52231), there is disclosed, as a technology for suppressing the heat generation caused by the joule heat of the coil, a magnetic stimulation apparatus having a magnetic flux compression unit in which the winding diameter of the winding-wire becomes smaller gradually.

For the magnetic field generating coils used for such apparatuses, there are used circular coils, figure-8 shaped coils and so on in case of air-core coils. In addition, in a case in which magnetic-body cores are used, there are used such as cores formed by winding conductive wires on rod-shaped cores, U-shaped or C-shaped magnetic cores and the like.

SUMMARY OF THE INVENTION

In case of any one of the abovementioned apparatuses, there is provided a single coil for generating the magnetic field and there is provided also a single pulse-shaped AC signal which is applied to that coil.

Therefore, the magnetic fields to be generated can be NS-reversed caused by the fact that the alternating current is applied, in which the directions of the changing magnetic fields are only positive direction and opposite direction, but it was impossible to let them be orthogonal, to let them incline as much as several-decades degrees and so on so long as the direction of the magnetic field generating-apparatus is not made to change.

On the other hand, a living-body tissue as an object to which the magnetic field is desired to apply spreads in the surface direction in many cases and, in addition, for the muscle tissue, the tissue is formed in a single direction. In order to magnetically stimulate those objects effectively, it is desirable to apply magnetic fields of all directions.

However, in a magnetic field generating-apparatus magnetic field generating-apparatus of the current status, there was such a big problem that it is not possible to apply the magnetic field by continuously changing the directions of the magnetic field.

The present invention was invented in view of the problem as mentioned above and is to provide a magnetic field generating-apparatus for biostimulation in which it is possible to apply magnetic fields of different directions with respect to the living body.

According to the present invention, there is provided a magnetic field generating-apparatus for biostimulation including: a core formed by a magnetic material; and coils wound around portions of the cores, wherein the core includes at least two pairs of leg portions which are juxtaposed each other, in which for the respective two pairs of leg portions, there are provided gap-portions which mutually cross each other, the coils include first coil portions and second coil portions forming a first magnetic-path and a second magnetic-path between the two pairs of leg portions and the gap-portions respectively; and wherein depending on the first coil portions and one pair of leg portions, there is generated a magnetic field of first direction which lies on the first magnetic-path, depending on the second coil portions and the other pair of leg portions, there is generated a magnetic field of second direction which lies on the second magnetic-path, and depending on a magnetic field formed by synthesizing the magnetic field of first direction and the magnetic field of second direction, a living body is stimulated.

According to the present invention, it is possible to provide a magnetic field generating-apparatus for biostimulation in which it is possible to apply magnetic fields of different directions with respect to the living body.

DESCRIPTION OF THE PREFERRED EMBODIMENTS

Figure 1:
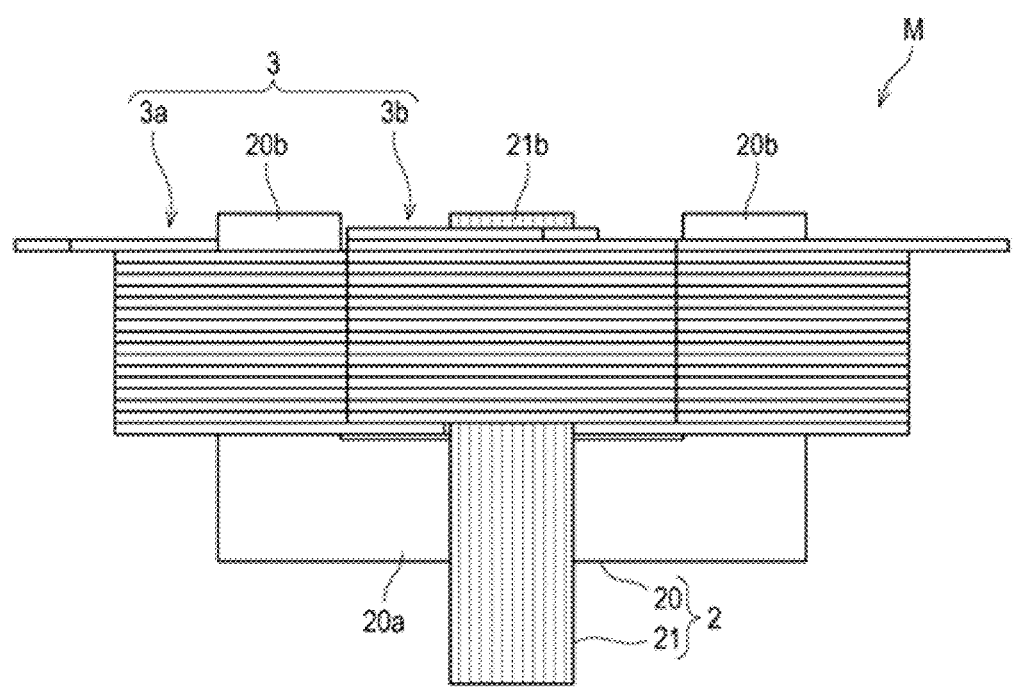
FIG. 1 is a front elevational view of a magnetic field forming unit relating to an exemplified embodiment of the present invention.

Hereinafter, there will be explained exemplified embodiments of the present invention based on the drawings.

It should be noted that the exemplified embodiment explained hereinafter is only one example for making the understanding of the present invention easy and is not provided to limit the scope of the present invention. More specifically, with regard to the shape, the size, the arrangement and the like explained hereinafter, it is possible to change or improve them without departing from the gist of the present invention and also it is needless to say that the equivalents thereof will fall into the scope of the present invention.

In addition, in the all drawings, like reference numerals are applied to like constituents and repetitive explanations thereof will be appropriately omitted. In addition, in the present specification, there is a case in which the explanation is carried out by specifying the up and down directions, but this is to be set for convenience in order to explain the relative relation of the constituents and is not for limiting the directions when manufacturing or using the product relating to the present invention.

Outline

Figure 2:
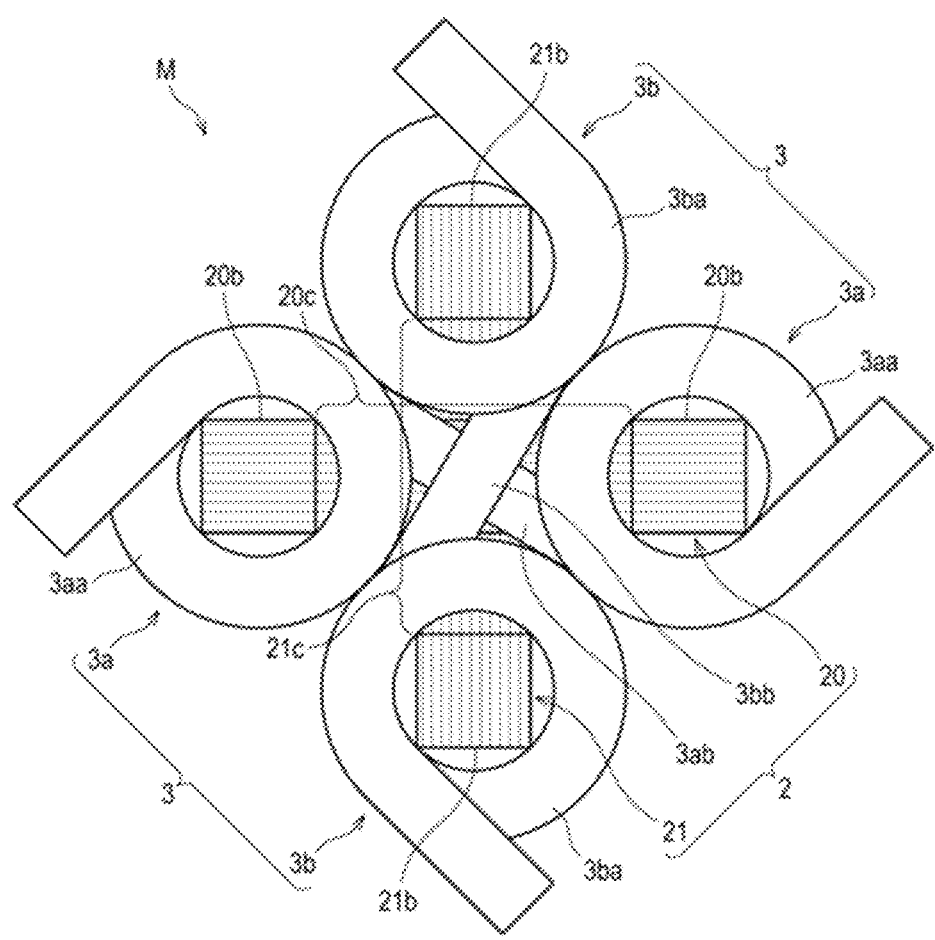
FIG. 2 is a plan view of the magnetic field forming unit.

First, there will be explained the outline of a magnetic field generating-apparatus (magnetic field generating-apparatus for biostimulation) 1 relating to the present exemplified embodiment mainly with reference to FIG. 1 and FIG. 2. FIG. 1 is a front elevational view of a magnetic field forming unit M relating to an exemplified embodiment of the present invention, and FIG. 2 is a plan view of the magnetic field forming unit M.

The magnetic field generating-apparatus for biostimulation (magnetic field generating-apparatus 1) relating to the exemplified embodiment of the present invention includes cores 2 formed by magnetic material and coils 3 wound around portions of the cores 2 (leg portions 20$b$ and leg portions 21$b$).

The cores 2 include at least two pairs of leg portions 20$b$, 21$b$ which are juxtaposed each other.

For the respective two pairs of leg portions 20$b$, 21$b$, there are provided gap-portions 20$c$, 21$c$ which mutually cross each other.

The coils 3 include first coil portions 3$a$ and second coil portions 3$b$ forming a first magnetic-path and a second magnetic-path between the two pairs of leg portions 20$b$, 21$b$ and the gap-portions 20$c$, 21$c$ respectively.

Depending on the first coil portions 3$a$ and one pair of leg portions 20$b$, there is generated a magnetic field of first direction (X-direction shown in FIG. 3) which lies on the first magnetic-path, and depending on the second coil portions 3$b$ and the other pair of leg portions 21$b$, there is generated a magnetic field of second direction (Y-direction shown in FIG. 3) which lies on the second magnetic-path. Then, it is characterized that a living body is stimulated depending on a magnetic field formed by synthesizing the magnetic field of first direction and the magnetic field of second direction.

Here, for the wording "there is generated a magnetic field", it is enough if there is an ability of generating a magnetic field and it is enough even if it is not in a state of actually generating a magnetic field.

In addition, for the wording "synthesizing", it is assumed that the "synthesizing" is established also in a case in which either one magnetic field within the magnetic field of first direction and the magnetic field of second direction is zero. In other words, in this case, the other magnetic field will become equal to the synthesized magnetic field.

According to the abovementioned constitution, it is possible to stimulate a living body depending on the synthesized magnetic fields of various kinds of directions at the gap-portion by adjusting the strengths of the magnetic field of first direction and the magnetic field of second direction.

In other words, by adjusting the strength of the magnetic field of first direction and the strength of the magnetic field of second direction, it is possible, without moving the apparatus itself, to change the direction of the applied magnetic field while maintaining the abutting state of the cores 2 with respect to the living body. For this reason, in a state of arranging the cores 2 at a deeper position of the living body after digging the end surfaces of cores 2 into the skin, it is possible to change the direction of the applied magnetic field.

Then, by applying magnetic fields of various kinds of directions to the inside of the living body, it is possible to suitably stimulate nerve cells which extend toward arbitrary directions depending on the induced electric currents generated inside the living body.

It should be noted that it is possible to employ a constitution of including three pairs of leg portions and coils wound therearound, in which there is generated a magnetic field vertical to the both of the magnetic field of first direction and the magnetic field of second direction and in which by synthesizing those generated magnetic fields, the position of the magnetic field in the depth direction with respect to the living body is made changeable.

Constitution

Figure 3:
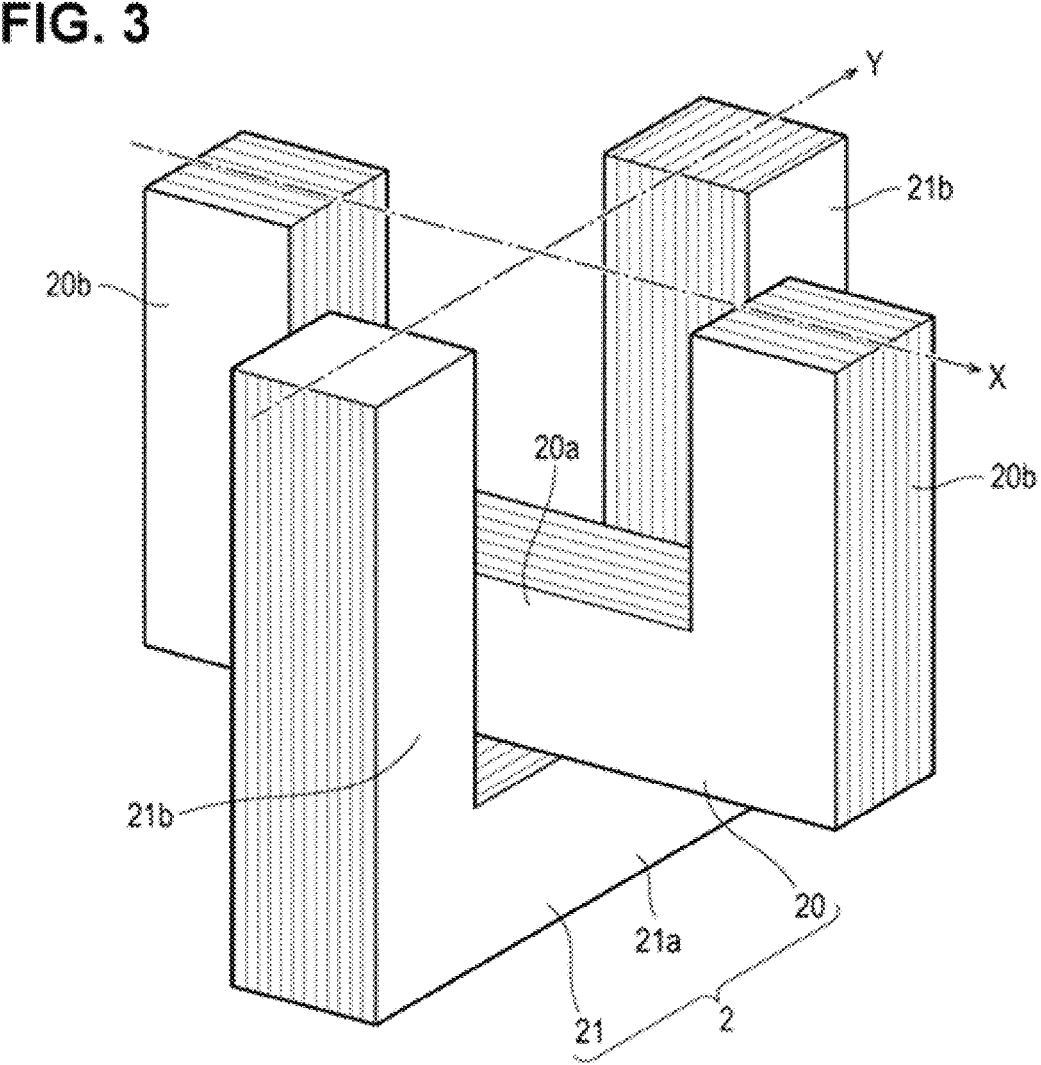
FIG. 3 is an upper-side perspective view of cores.
Figure 4:
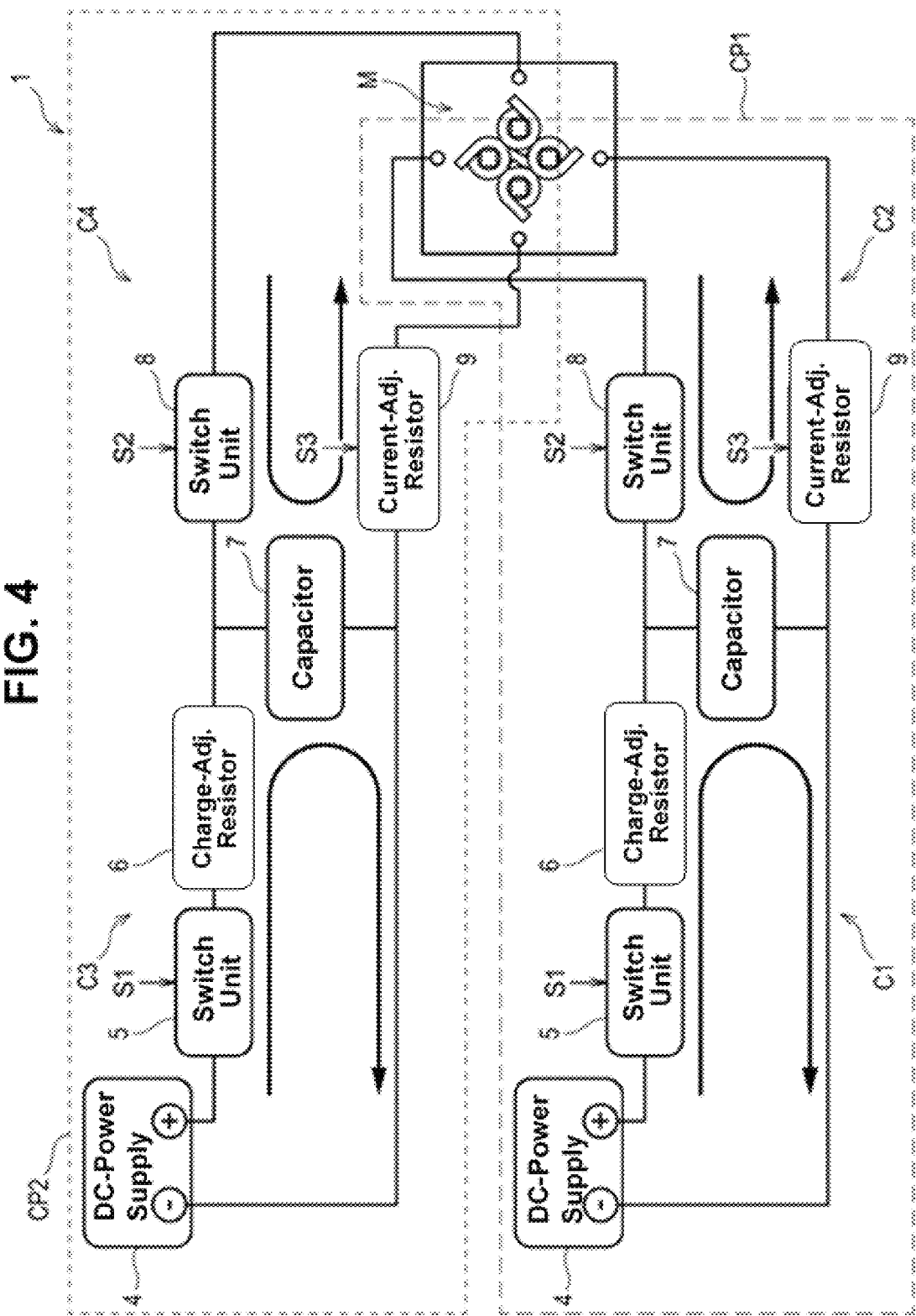
FIG. 4 is an explanatory diagram for explaining a constitution of a magnetic field generating-apparatus.

There will be explained the constitutions of the magnetic field forming unit M relating to the present exemplified embodiment and of the magnetic field generating-apparatus for biostimulation (magnetic field generating-apparatus 1) which includes the magnetic field forming unit M mainly with reference to FIG. 3 and FIG. 4 in addition to FIG. 1 and FIG. 2. FIG. 3 is an upper-side perspective view of the cores 2, and FIG. 4 is an explanatory diagram for explaining a constitution of the magnetic field generating-apparatus 1.

(With Regard to Magnetic Field Forming Unit)

The magnetic field forming unit M is a portion forming magnetic field caused by the alternating currents which are supplied from power supply circuits CP1, CP2 described later, and as shown in FIG. 1 and FIG. 2, it is constituted by the cores 2 and the coils 3 wound around portions of the cores 2.

(With Regard to Cores)

As shown in FIG. 2, the cores 2 are objects which guide the magnetic fluxes generated from the coil 3 to gap-portions 20c, 21c and which generate magnetic fluxes at the gap-portions 20c, 21c. The cores 2 relating to the present exemplified embodiment include different sized two angular U-shaped first core unit 20 and second core unit 21.

Each of the first core unit 20 and the second core unit 21 as one example relating to the present exemplified embodiment has a configuration in which electrical steel-sheets constituted by magnetic material are laminated and bonded by adhesive agent.

As shown in FIG. 3, the cores 2 (respective first core unit 20 and second core unit 21) include respective pairs of (total two pairs of) leg portions (20b, 21b) and connecting portions (20a, 21a) which mutually connect the respective pairs of leg portions (20b, 21b).

The connecting portions 20a, 21a for the two pairs of leg portions 20b, 21b are arranged at mutually twisted positions, and the end surfaces of the two pairs of leg portions 20b, 21b lie on the same plane. Here, the wording "the end surfaces of the two pairs of leg portions 20b, 21b" means portions which emit magnetic fluxes and means end surfaces (top surfaces in the present exemplified embodiment) which lie on the opposite sides of the connecting portions 20a, 21a of the leg portions 20b, 21b and which extend toward the direction crossing the extending (winding-axis) direction of the leg portions 20b, 21b.

To say this configuration in other words, the gap-portions 20c, 21c which are shown in FIG. 2 and which lie between the end-portions of the two pairs of leg portions 20b, 21b are provided in the same hypothetical flat plate-shapes, and also, the first core unit 20 and the second core unit 21 are combined such that the respective gap directions become orthogonal to each other.

As shown in FIG. 3, by making the direction connecting the upper end-portions of the pair of leg portions 20b be X-direction as first direction and by making the direction connecting the upper end-portions of the pair of leg portions 21b be Y-direction as second direction, the explanations thereof will be carried out later on.

It should be noted that the X-direction as the first direction and the Y-direction as the second direction, which relate to the present exemplified embodiment, are made to be orthogonal, but the present invention is not limited by such a configuration and it is enough if the first direction and the second direction cross each other at the gap-portions 20c, 21c and it is possible to set the angle thereof arbitrary.

In this manner, for the reason that the connecting portion 20a, 21a are arranged at twisted positions each other and the end surfaces of the two pairs of leg portions 20b, 21b lie on the same plane, it becomes possible, while forming independent magnetic-paths, to carry out the control of the magnetic-field direction accurately by aligning the discharge portions of the magnetic fluxes within the same plane.

In particular, in a case in which the electrical steel-sheets are constituted by being laminated such as the cores 2 relating to the present exemplified embodiment, owing to the fact that the jointed interface formed by being bonded by adhesive agent becomes the gap, the magnetic flux can flow toward the surface direction of the electrical steel-sheets but the magnetic flux cannot flow toward the thickness direction thereof.

For this reason, by employing a configuration in which the connecting portion 20a of the first core unit 20 and the connecting portion 21a of the second core unit 21 do not magnetically-couple each other and the connecting portions 20a, 21a are arranged at twisted positions each other, it becomes possible to flow both of the magnetic fluxes.

By the fact that the cores 2 relating to the present exemplified embodiment are constituted by laminated electrical steel-sheets as mentioned above, it is possible to use electrical steel-sheets of general purpose and therefore, it is possible to manufacture the cores 2 at low cost.

It should be noted that the first core unit 20 and the second core unit 21 are not limited by the objects of angular U-shapes and, for example, it is allowed to employ objects of rounded U-shape or to employ objects of C-shapes which include end-portions extending from the upper end-portions of both the leg portions 20b, 21b toward the directions of narrowing the gap-portions 20c, 21c.

(With Regard to Coils)

As one example, the coils 3 are Edgewise-coils which are formed by insulation-coated copper wires of rectangular wires and the coils are constituted by first coil portions 3a wound around a pair of leg portions 20b of a first core unit 20 and by second coil portions 3b wound around a pair of leg portions 21b of a second core unit 21.

The first coil portions 3a are constituted by two pieces of spiral portions 3aa wound around a pair of leg portions 20b and a coupling portion 3ab which couples the bottom portions of the spiral portions 3aa. The first coil portions 3a are formed in figure-8 shapes seen by the bottom view by two pieces of spiral portions 3aa and a coupling portion 3ab. The two pieces of spiral portions 3aa have winding-wire directions in which the closed-loop directions of the magnetic-paths are same, and they are wound around the pair of leg portions 20b respectively as shown in FIG. 2.

Similarly, the second coil portions 3b are constituted by two pieces of spiral portions 3ba wound around a pair of leg portions 21b and a coupling portion 3bb which couples the bottom portions of the spiral portions 3ba. The second coil portions 3b are formed in figure-8 shapes seen by the bottom view by two pieces of spiral portions 3ba and a coupling portion 3bb. The two pieces of spiral portions 3ba have winding-wire directions in which the closed-loop directions of the magnetic-paths are same, and they are wound around the pair of leg portions 21b respectively as shown in FIG. 2.

In this manner, when the first coil portions 3a and the second coil portions 3b are wound around the leg portions 20b, 21b, it is possible to heighten the magnetic-flux density toward the outside of the end-portions of the leg portions 20b, 21b compared with a configuration of being wound around the connecting portion 20a, 21a and therefore, this configuration is suitable. However, there is no limitation by such a constitution and for the first coil portions 3a and the second coil portions 3b, it is enough if only it is possible to form magnetic-paths between the first core unit 20 or the second core unit 21, and it is allowed to employ a constitution of being wound around the connecting portions 20a, 21a.

(With Regard to the Whole Constitution)

In order to make it possible to supply alternating currents to the coils 3, the magnetic field generating-apparatus 1 includes 2-circuit power supply circuits CP1, CP2 provided with DC-power supplies 4 respectively and a control unit C which controls the supplies of the alternating currents. Each of the power supply circuits CP1, CP2 is constituted by a first circuit C1 (C3) connected with the DC-power supply 4 and a second circuit C2 (C4) connected with the magnetic field forming unit M.

For the first circuit C1 (C3), there are connected the DC-power supply 4, a switch unit 5 which switches on and off the electric-conduction inside the circuit connected to the DC-power supply 4, an adjusting resistor 6 which adjusts the magnitude of the charging current, and a charging capacitor 7.

The second circuit C2 (C4) is an LC circuit, and there are connected the capacitor 7, a switch unit 8 which switches on and off the electric-conduction inside the circuit connected to the capacitor 7, and an adjusting resistor 9 which adjusts the magnitude of the electric current supplied to the magnetic field forming unit M.

As an activation method of the magnetic field generating-apparatus 1, first, the control unit C turns on the switch units 5 which are provided for the power supply circuits CP1, CP2 and the capacitors 7 are charged to the specified voltages by the first circuits (C1, C3). If the charging to the capacitor 7 are completed, the switch units 5 are turned off.

Next, the switch units 8 are turned on and the electricity charged in the capacitors 7 are discharged through the coils 3 of the magnetic field forming unit M. Electric currents of LC resonances flow repeatedly in the second circuits (C2, C4) and it becomes that the magnetic fields are emitted from the coils 3 (from the magnetic field forming unit M).

(With Regard to Control Unit)

Next, there will be explained the function of the control unit C mainly with reference to FIG. 5 and FIG. 6 in addition to FIG. 4.

Figure 5:
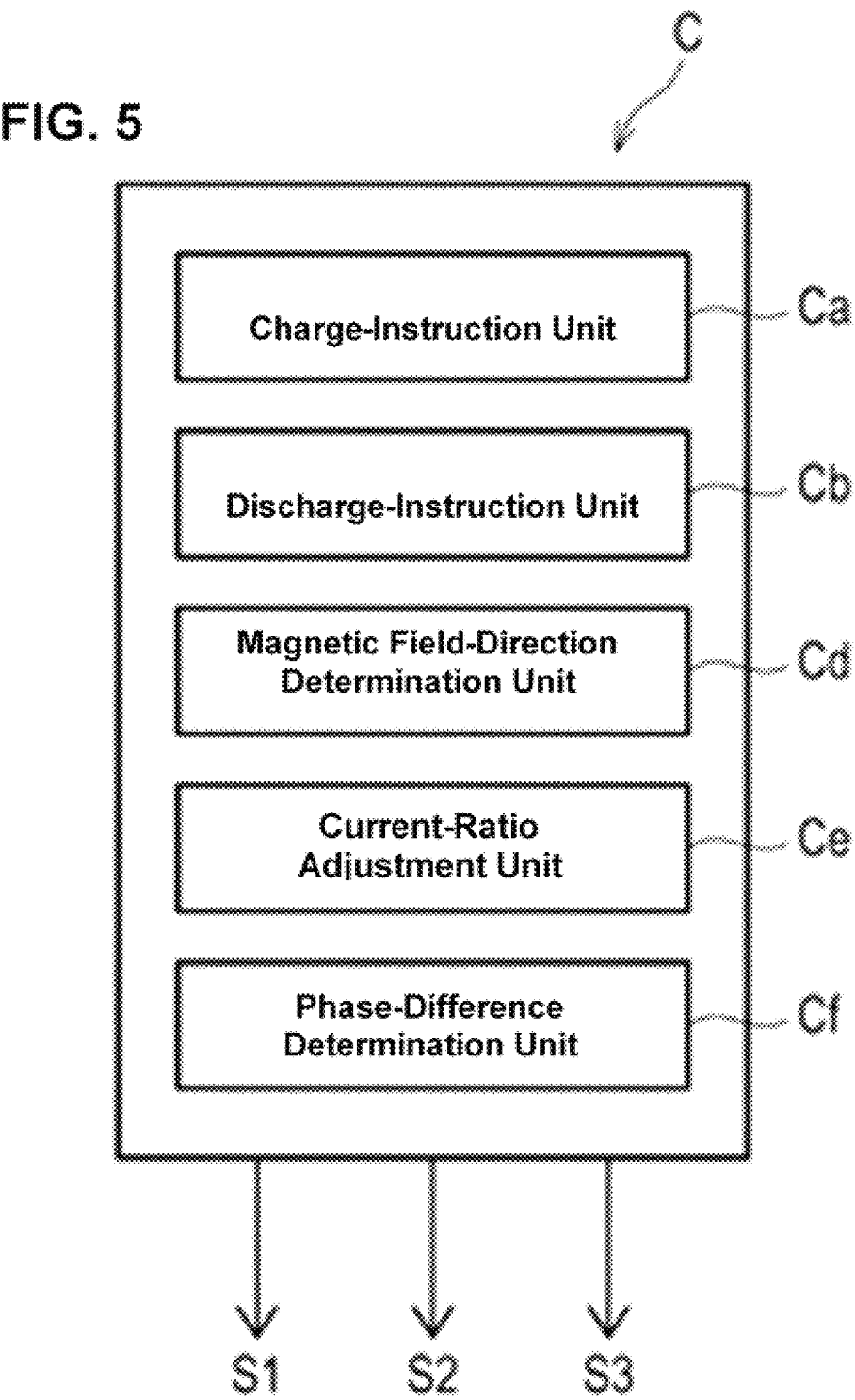
FIG. 5 is a functional diagram of a control unit.
Figure 6:
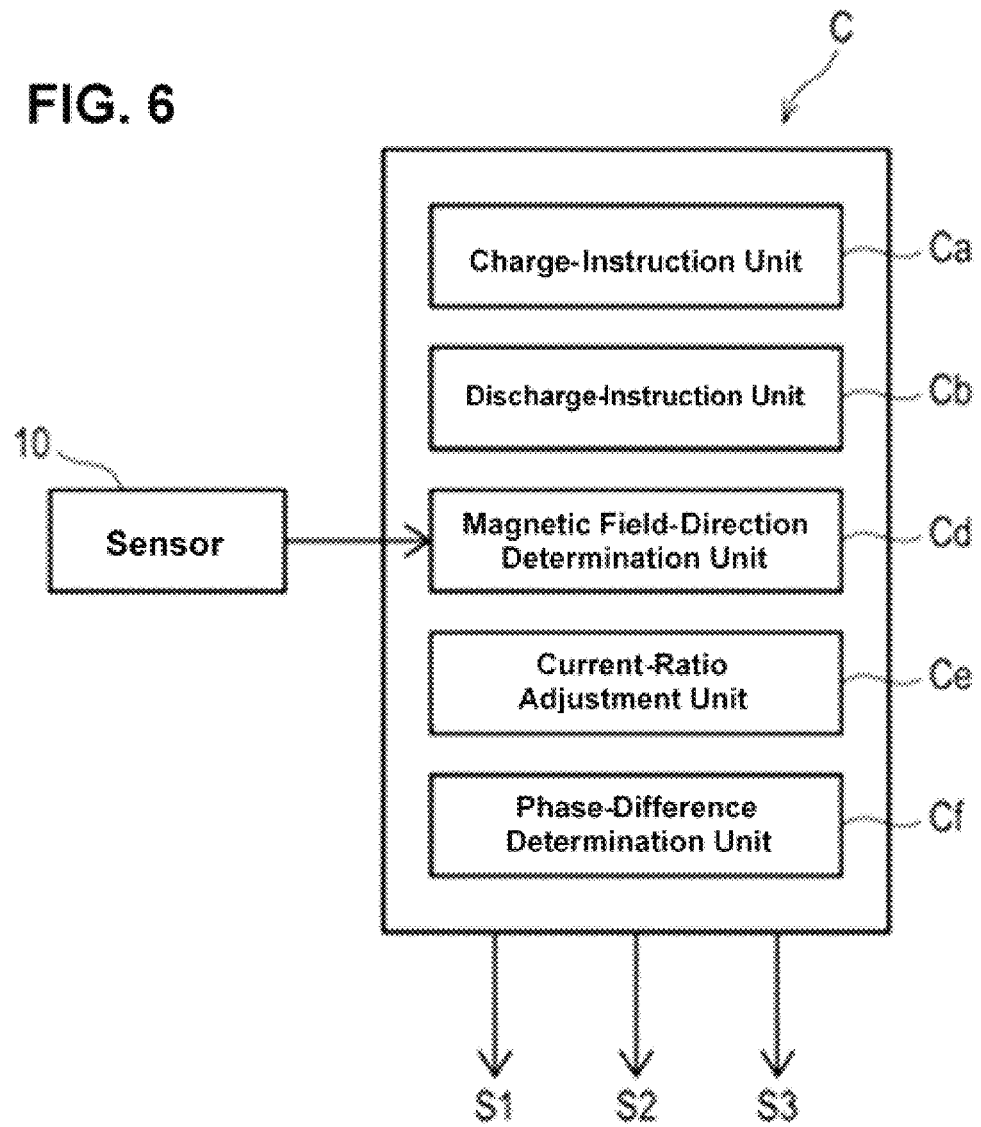
FIG. 6 is a functional diagram of the control unit which has a function of determining a magnetic field direction based on the electric-potential detected by a muscle electric-potential sensor.

FIG. 5 is a functional diagram of the control unit C, and FIG. 6 is a functional diagram of the control unit C which has a function of determining a magnetic field direction based on the electric-potential detected by a muscle electric-potential sensor 10.

The control unit C relating to the present exemplified embodiment includes a charge-instruction unit Ca, a discharge-instruction unit Cb, a magnetic field-direction determination unit Cd, a current-ratio adjustment unit Ce, and a phase-difference determination unit Cf.

The charge-instruction unit Ca has a function of transmitting a signal S1 with respect to the switch units 5 and instructing the charging and stop-charging to the capacitors 7.

The discharge-instruction unit Cb has a function of transmitting a signal S2 with respect to the switch units 8 and instructing the discharging and stop-discharging to the magnetic field forming unit M.

The magnetic field-direction determination unit Cd determines the directions of the magnetic fields at the gap-portions 20c, 21c.

The current-ratio adjustment unit Ce has a function of adjusting the current ratio with respect to the portions 3a and the second coil portions 3b based on the magnetic field directions which were determined by the magnetic field-direction determination unit Cd. Specifically, the current-ratio adjustment unit Ce adjusts the ratio of the currents flowing through the first coil portions 3a and the second coil portions 3b depending on the configuration of transmitting a signal S3 of adjusting the resistance values of the adjusting resistors 9 which are provided in the power supply circuits CP1 and the power supply circuit CP2 respectively.

The phase-difference determination unit Cf determines the phase difference of the voltages with respect to the first coil portions 3a and the second coil portions 3b based on the magnetic field directions which were determined by the magnetic field-direction determination unit Cd.

In particular, it is possible for the control unit C, by using the current-ratio adjustment unit Ce, to control the ratio between the magnitude of the alternating current supplied from the power supply circuit CP1 to the first coil portions 3a and the magnitude of the electric current supplied from the power supply circuit CP2 to the second coil portions 3b.

In this manner, by a configuration that the control unit C controls the ratio between the magnitude of the alternating current supplied to the first coil portions 3a and the magnitude of the alternating current supplied to the second coil portions 3b, it is possible to adjust the direction of the magnetic field as mentioned later on.

In particular, the output of one power supply circuit CP1 is connected to the first coil portions 3a which are one of the first coil portions 3a and the second coil portions 3b, and the output of the other power supply circuit CP2 is connected to the second coil portions 3b which are the other of the first coil portions 3a and the second coil portions 3b.

In this manner, for the reason that there are provided with 2-pole power supply circuits (CP1, CP2), it becomes possible for the field generating-apparatus 1 to supply large currents simultaneously with respect to the first coil portions 3a and the second coil portions 3b.

It should be noted in the present exemplified embodiment that the supplied amounts of the electric currents to the first coil portions 3a and the second coil portions 3b are adjusted depending on the 2-circuit power supply circuits CP1 and CP2 which are provided with the DC-power supplies 4 respectively, but it is not limited by such a constitution. For example, it is allowed to employ a constitution of distributing the supplies of the electric currents to the first coil portions 3a and the second coil portions 3b in a 1-circuit power supply circuit which is provided with a single DC-power supply 4.

As shown in FIG. 6, it is allowed for the magnetic field generating-apparatus 1 to be further provided with a sensor (muscle electric-potential sensor 10) which detects the electric-potential inside the living body (electric-potential of nerve cell such as muscle electric-potential or the like).

For example, the control unit C controls the ratio between the electric current supplied to the first coil portions 3a and the electric current supplied to the second coil portions 3b by a feed-back control depending on the current-ratio adjustment unit Ce based on the electric-potential detected by the sensor (muscle electric-potential sensor 10).

In this manner, by the fact that the control unit C carries out the feed-back control, it is possible to suitably apply stimulations with respect to a plurality of nerve fibers extending toward every direction by changing the direction.

With Regard to Directions of Magnetic Fields

Next, there will be explained the changes of the directions of the magnetic fluxes with respect to the voltage ratios applied to the first coil portions 3a and the second coil portions 3b with reference to FIG. 7A to FIG. 13B.

Figure 7A:
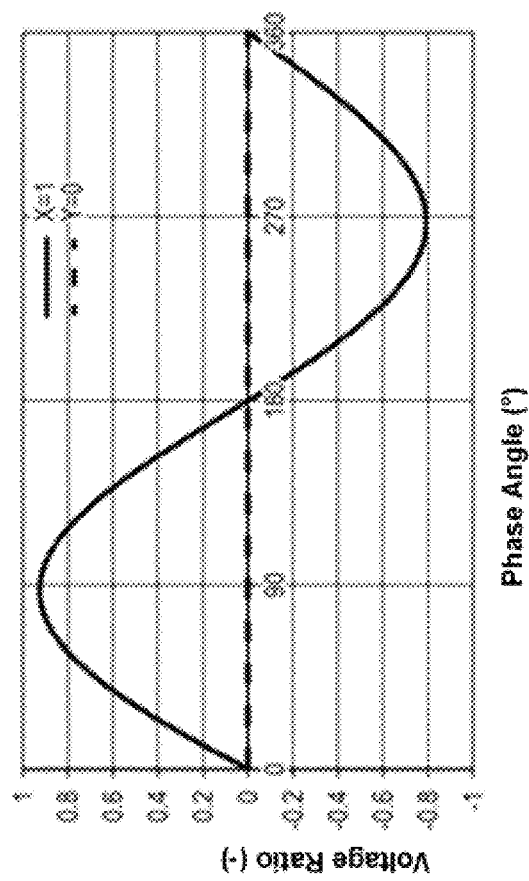
FIG. 7A is a diagram showing a relation between the voltage ratio and the phase angle when applying AC voltage of positive direction only for first coil portions.
Figure 7B:
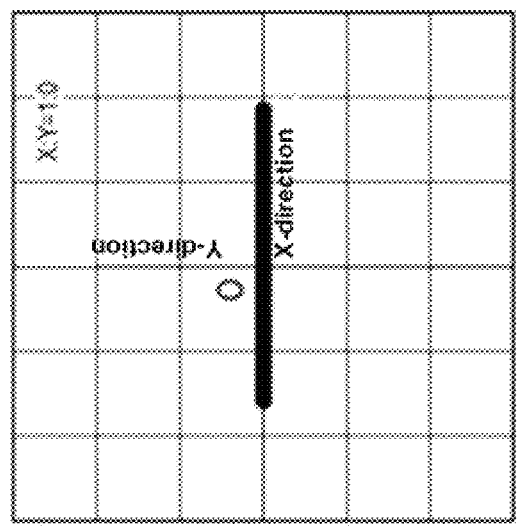
FIG. 7B is a diagram showing a synthesized magnetic field at the gap-portions.

FIG. 7A is a diagram showing a relation between the voltage ratio and the phase angle when applying AC voltage of positive direction only for the first coil portions 3a, and FIG. 7B is a diagram showing a synthesized magnetic field at the gap-portions 20c, 21c.

Figure 8A:
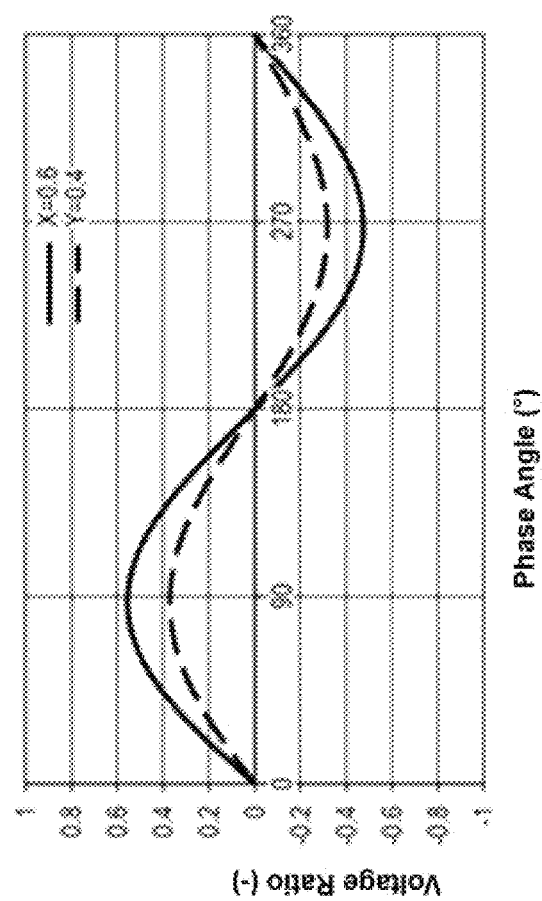
FIG. 8A is a diagram showing a relation between the voltage ratio and the phase angle when applying different-sized AC voltages to the first coil portions and the second coil portions.
Figure 8B:
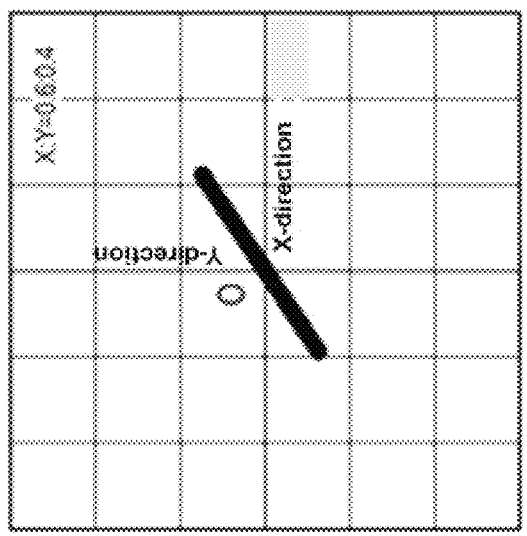
FIG. 8B is a diagram showing a synthesized magnetic field at the gap-portions.

FIG. 8A is a diagram showing a relation between the voltage ratio and the phase angle when applying different-sized AC voltages to the first coil portions 3a and the second coil portions 3b, and FIG. 8B is a diagram showing a synthesized magnetic field at the gap-portions 20c, 21c.

Figure 9A:
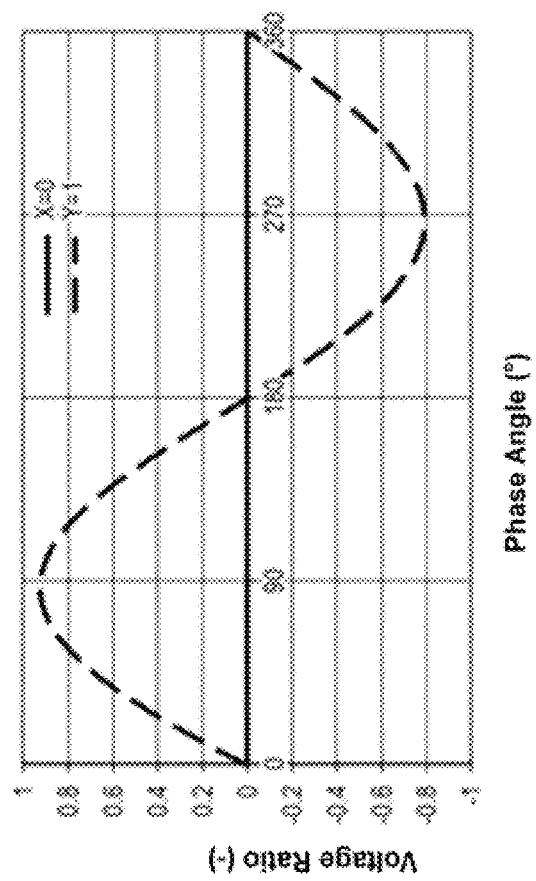
FIG. 9A is a diagram showing a relation between the voltage ratio and the phase angle when applying AC voltage to the second coil portions.
Figure 9B:
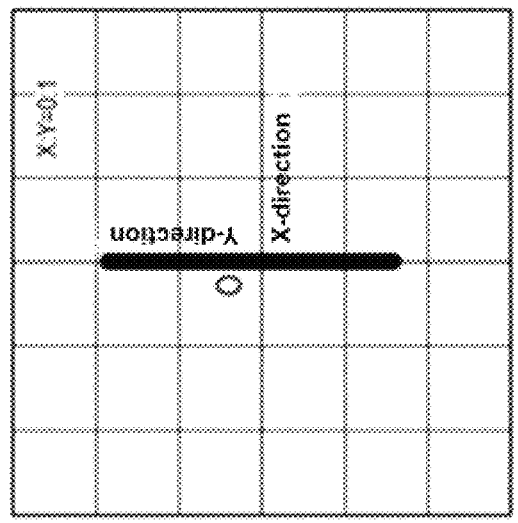
FIG. 9B is a diagram showing a synthesized magnetic field at the gap-portions.

FIG. 9A is a diagram showing a relation between the voltage ratio and the phase angle when applying AC voltage to the second coil portions 3b, and FIG. 9B is a diagram showing a synthesized magnetic field at the gap-portions 20c, 21c.

Figure 10B:
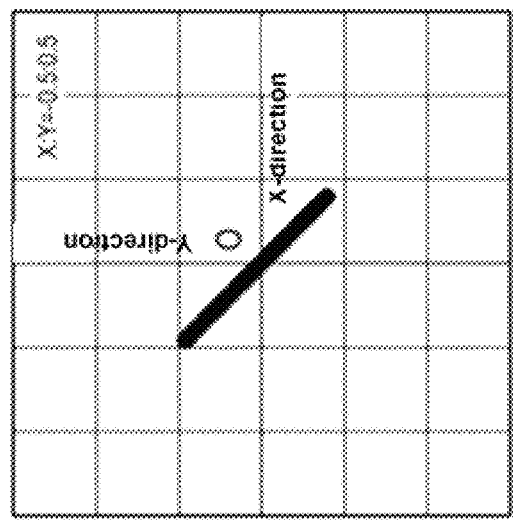
FIG. 10B is a diagram showing a synthesized magnetic field at the gap-portions.
Figure 10A:
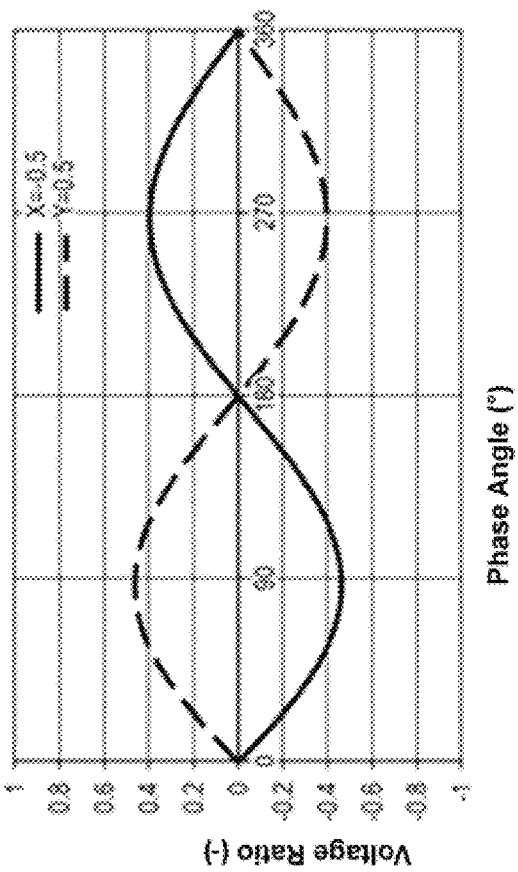
FIG. 10A is a diagram showing a relation between the voltage ratio and the phase angle when applying AC voltages, whose phase angles are different by 180 degrees, to the first coil portions and the second coil portions.

FIG. 10A is a diagram showing a relation between the voltage ratio and the phase angle when applying AC voltages, whose phase angles are different by 180 degrees, to the first coil portions 3a and the second coil portions 3b, and FIG. 10B is a diagram showing a synthesized magnetic field at the gap-portions 20c, 21c.

Figure 11A:
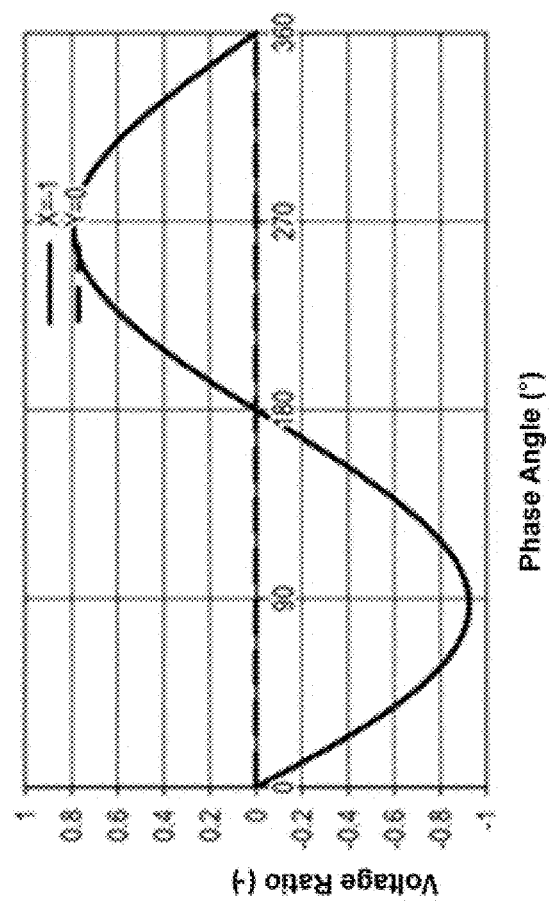
FIG. 11A is a diagram showing a relation between the voltage ratio and the phase angle when applying AC voltage of opposite direction only to the first coil portions.
Figure 11B:
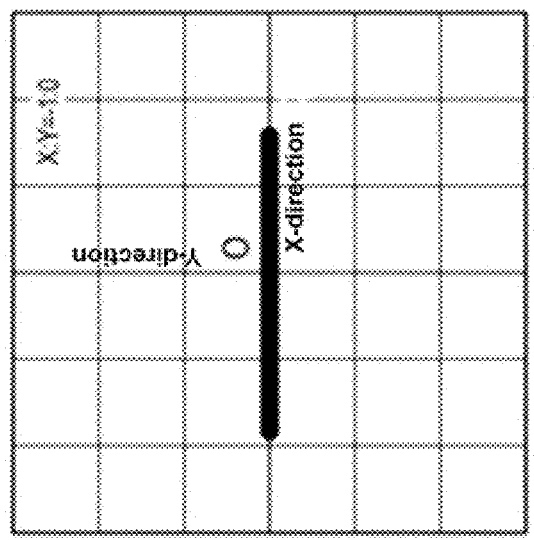
FIG. 11B is a diagram showing a synthesized magnetic field at the gap-portions.

FIG. 11A is a diagram showing a relation between the voltage ratio and the phase angle when applying AC voltage of opposite direction only to the first coil portions 3a, and FIG. 11B is a diagram showing a synthesized magnetic field at the gap-portions 20c, 21c.

Figure 12A:
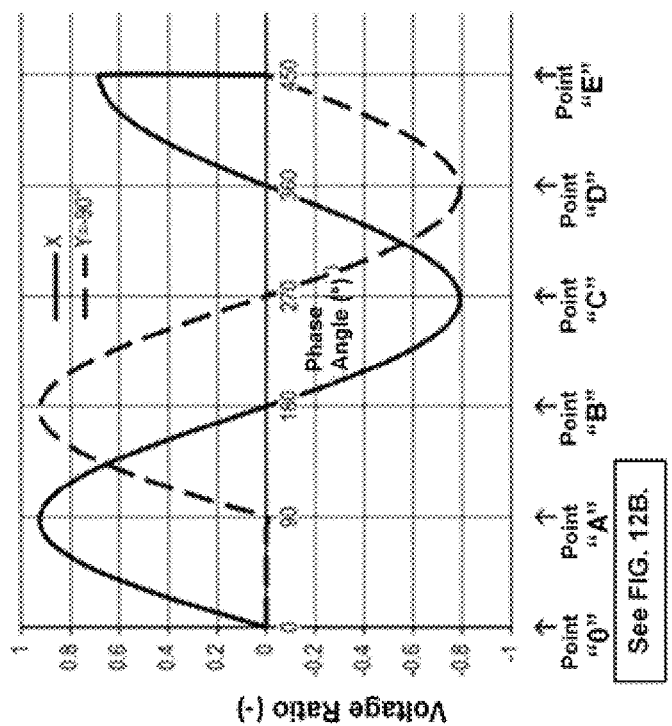
FIG. 12A is a diagram showing a relation between the voltage ratio and the phase angle when applying AC voltages, whose phase angles are different by 90 degrees, to the first coil portions and the second coil portions.
Figure 12B:
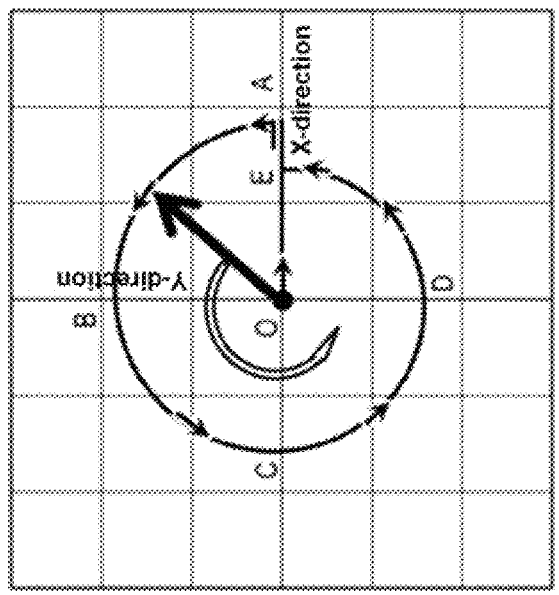
FIG. 12B is a diagram showing a synthesized magnetic field at the gap-portions.

FIG. 12A is a diagram showing a relation between the voltage ratio and the phase angle when applying AC voltages, whose phase angles are different by 90 degrees, to the first coil portions 3a and the second coil portions 3b, and FIG. 12B is a diagram showing a synthesized magnetic field at the gap-portions 20c, 21c.

Figure 13A:
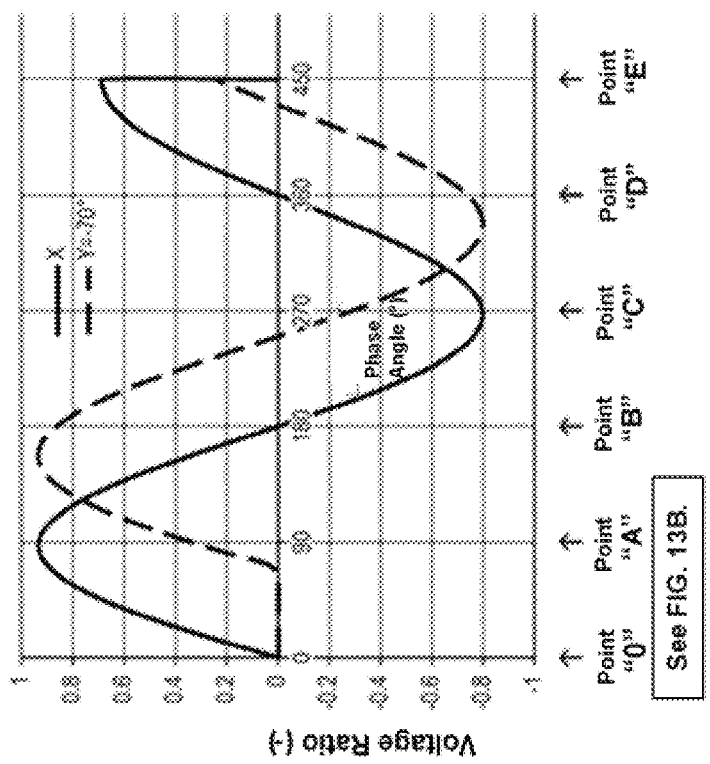
FIG. 13A is a diagram showing a relation between the voltage ratio and the phase angle when applying AC voltages, whose phase angles are different by 70 degrees, to the first coil portions and the second coil portions.
Figure 13B:
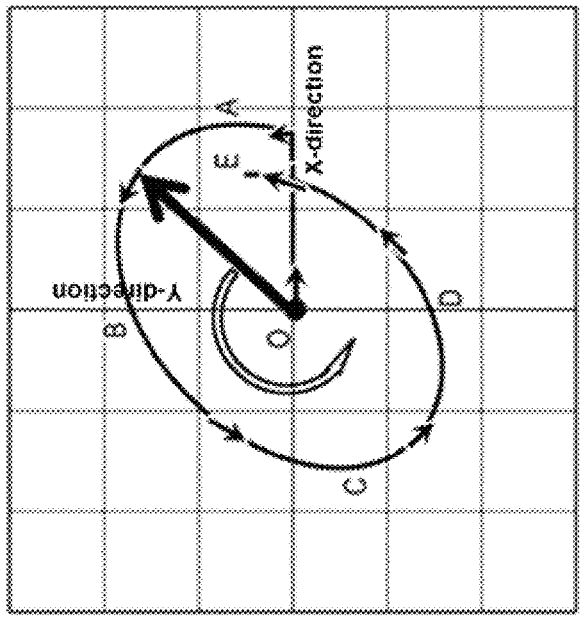
FIG. 13B is a diagram showing a synthesized magnetic field at the gap-portions.

FIG. 13A is a diagram showing a relation between the voltage ratio and the phase angle when applying AC voltages, whose phase angles are different by 70 degrees, to the first coil portions 3a and the second coil portions 3b, and FIG. 13B is a diagram showing a synthesized magnetic field at the gap-portions 20c, 21c.

As seen from the abovementioned diagrams, the voltage generated in the coils 3 attenuate as the phase angle becomes larger. That is because, in the present exemplified embodiment, in order to supply the electric current lower than the alternating current from the AC-power supply toward the coils 3, there is employed a method of charging electric currents from the DC-power supplies 4 to the capacitors 7 and supplying electric currents to the coils 3 by the discharges thereof.

It should be noted that in a case in which the magnitudes of the electric currents applied to the coils 3 cause no problems, it is allowed to employ a configuration of directly connecting the AC-power supplies to the magnetic field forming unit M.

In a case in which the control unit C switches the switch unit 8 so as to set the electric-conduction of the power supply circuit CP1 to become "ON" depending on the discharge-instruction unit Cb while maintaining the electric-conduction of the power supply circuit CP2 in an "OFF" state, as shown in FIG. 7A, the AC voltage is generated only in the X-direction and the AC voltage is not generated in the Y-direction. In this case, as shown in FIG. 7B, it becomes that at the gap-portions 20c, 21c, reciprocated magnetic fluxes (synthesized magnetic field) are generated at the gap-portions 20c, 21c only in the X-direction.

In addition, caused by the fact that the control unit C transmits the signal S3 to the adjusting resistor 9 by the current-ratio adjustment unit Ce, the resistance values of the adjusting resistors 9 of the power supply circuits CP1, CP2 are adjusted and the voltage ratio (current ratio) is adjusted. As one example, the voltage ratio (current ratio) between the first coil portions 3a in the X-direction and the second coil portions 3b in the Y-direction is made to be 0.6:0.4. Then, caused by the fact that the control unit C transmits the signal S to the switch units 8 by the discharge-instruction unit Cb, the switch units 8 are switched so as to set the electric-conduction of the power supply circuits CP1, CP2 to become "ON". Then, as shown in FIG. 8A, AC voltages are generated in the X-direction and in the Y-direction, in which the ratio thereof becomes 0.6:0.4. In this case, as shown in FIG. 8B, it becomes that reciprocated magnetic fluxes (synthesized magnetic field) are generated at the gap-portions 20c, 21c by being inclines from the X-direction as much as an angle of approximately 34 degrees ($\tan^{-1}(0.4/0.6)$).

In addition, in a case in which the control unit C switches the switch unit 8 so as to set the electric-conduction of the power supply circuit CP2 to become "ON" depending on the discharge-instruction unit Cb while maintaining the electric-conduction of the power supply circuit CP1 in an "OFF" state, as shown in FIG. 9A, the AC voltage is generated only in the Y-direction and the AC voltage is not generated in the X-direction. In this case, as shown in FIG. 9B, it becomes that reciprocated magnetic fluxes (synthesized magnetic field) are generated only in the Y-direction at the gap-portions 20c, 21c.

In addition, it is supposed that the control unit C determines, depending on the phase-difference determination unit Cf, such that the phase difference of the AC voltage between the first coil portions 3a in the X-direction and the second coil portions 3b in the Y-direction is 180 degrees. In other words, it is supposed that the control unit C determines such that the voltage ratio between the first coil portions 3a in the X-direction and the second coil portions 3b in the Y-direction is -0.5:0.5. In this case, the control unit C transmits the signal S2 to the respective switch units 8 depending on the discharge-instruction unit Cb at the timing when the phase difference becomes 180 degrees (time difference of half cycle) and the switch units 8 are switched so as to set the electric-conduction of the power supply circuits CP1, CP2 to become "ON". In this case, as shown in FIG. 10A, AC voltages are generated in the X-direction and in the Y-direction, in which the ratio thereof becomes -0.5:0.5. In other words, there are generates AC voltages, whose phase angles are deviated by 180 degrees, in the X-direction and the Y-direction.

In this case, as shown in FIG. 10B, it becomes that reciprocated magnetic fluxes (synthesized magnetic field) are generated at the gap-portions 20c, 21c by being inclines from the X-direction as much as an angle of approximately 45 degrees.

As shown in FIG. 10, by making the phase of the voltage applied to the first coil portions 3a and the phase of the voltage applied to the second coil portions 3b different from each other, it is possible to apply more variety of magnetic field stimulations with respect to a living body.

In addition, in a case in which after setting a condition such that the reversed AC voltage is generated only in the X-direction depending on the phase difference determined by the phase-difference determination unit Cf, the control unit C switches the switch unit 8 depending on the discharge-instruction unit Cb so as to set the electric-conduction of the power supply circuit CP1 to become "ON", as shown in FIG. 11A, the reversed AC voltage is generated only in the X-direction and the AC voltage does is not generated in the Y-direction. In this case, as shown in FIG. 11B, it becomes that at the gap-portions 20c, 21c, reciprocated magnetic fluxes (synthesized magnetic field) are generated at the gap-portions 20c, 21c by being reversed only in the X-direction.

As mentioned above, there are provided 2-circuits of power supply circuits (power supply circuits CP1, CP2) which generate impulse-shaped alternating currents and the respective outputs thereof are connected to the first coil portions 3a (X-direction) and the second coil portions 3b (Y-direction). By controlling the respective on and off of the outputs of the power supply circuits CP1, CP2, it is possible to change the synthesized magnetic field with respect to the X-direction from 0 degree (X:Y=1:0) to 90 degrees (X:Y=0:1). Further, by reversing either one of the phases, by adjusting the voltage ratio by operating the adjusting resistor 9 or the like, it is possible to change the synthesized magnetic field with respect to the X-direction from 90 degrees (X:Y=0:1) or more up to 180 degrees (X:Y=−1:0). The magnetic fields are AC magnetic fields and therefore, if the angle is changeable from 0 degree to 180 degrees, it is possible to cover all directions.

In addition, it is supposed that the control unit C determines, depending on the phase-difference determination unit Cf, such that the phase difference of the AC voltage between the first coil portions 3a in the X-direction and the second coil portions 3b in the Y-direction is 90 degrees. In this case, the control unit C transmits the signal S2 to the respective switch units 8 depending on the discharge-instruction unit Cb at the timing when the phase difference becomes 90 degrees (time difference of one-quarter cycle) and the switch units 8 are switched so as to set the electric-conduction of the power supply circuits CP1, CP2 to become "ON". In this case, as shown in FIG. 12A, the AC voltages are generated in the X-direction and in the Y-direction.

In this case, as shown in FIG. 12B, it becomes that there is generated the magnetic flux, whose diameter is reduced by the attenuation caused by the discharging from the capacitor 7, at the gap-portions 20c, 21c while the direction thereof varies spirally.

In addition, it is supposed that the control unit C determines, depending on the phase-difference determination unit Cf, such that the phase difference of the AC voltage between the first coil portions 3a in the X-direction and the second coil portions 3b in the Y-direction is 70 degrees. In this case, the control unit C transmits the signal S2 to the switch units 8 depending on the discharge-instruction unit Cb at the timing when the phase difference becomes 70 degrees and the switch units 8 are switched so as to set the electric-conduction of the power supply circuits CP1, CP2 to become "ON". In this case, as shown in FIG. 13A, the AC voltages are generated in the X-direction and in the Y-direction.

In this case, as shown in FIG. 13B, it becomes that there is generated the magnetic flux, whose diameter is reduced by the attenuation caused by the discharging from the capacitor 7, at the gap-portions 20c, 21c while the direction thereof varies spirally. Caused by the phase difference, when compared with the shape of the magnetic flux shown in FIG. 12B, the magnetic flux of FIG. 13B has larger values in the first quadrant and in the third quadrant, while on the other hand, the magnetic flux thereof has smaller values in the second quadrant and in the fourth quadrant. According to such a constitution, it is possible to change the area, to which the magnetic stimulation is applied, suitably in conformity with the area to which the stimulation is desired to be applied.

As shown in FIG. 12 and FIG. 13A and FIG. 13B, caused by a configuration that the AC voltage in the X-direction and the AC voltage in the Y-direction are made to have different phases and the absolute value of the phase difference thereof is made to be an arbitrary value less than 180 degrees, it is possible to apply a magnetic field stimulation to a living body along a spiral shaped locus. In other words, caused by a configuration that the absolute value of the phase difference between the AC voltage in the X-direction and the AC voltage in the Y-direction is made to have a value other than 0 degree or 180 degrees, it is possible to apply a magnetic field stimulation to a living body along a spiral shaped locus.

According to the magnetic field generating-apparatus 1 relating to the abovementioned exemplified embodiment, it is possible to apply magnetic fields of various directions easily with respect to the plane of an object to which the magnetic field is applied only by the control of the power supply circuits without moving the magnetic field generating-apparatus 1. Then, for the reason that the magnetic field can be applied in all directions on the plane, it is possible to apply the magnetic field evenly with respect to an object-tissue to which the magnetic field is applied and it is possible to maximize the effect of the magnetic field application.

First Modified Example

The cores 2 of the magnetic field forming unit M relating to the abovementioned exemplified embodiment are constituted by combining an angular U-shaped first core unit 20 and a second core unit 21, but the present invention is not limited by the cores having such a constitution.

Figure 14:
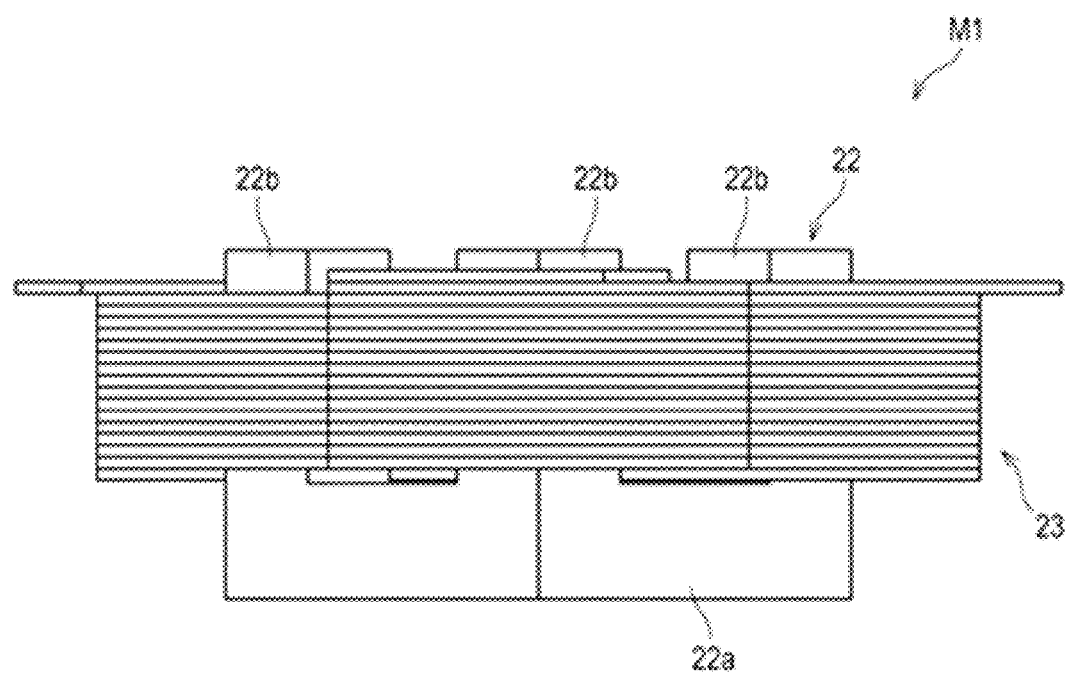
FIG. 14 is a front elevational view of a magnetic field forming unit relating to a first modified example.

Next, there will be explained a magnetic field forming unit M1 provided with a core 22, which relates to a first modified example, mainly with reference to FIG. 14 to FIG. 16. FIG. 14 is a front elevational view of the magnetic field forming unit M1 relating to the first modified example, FIG. 15 is a plan view of the magnetic field forming unit M1 relating to the first modified example and FIG. 16 is an upper-side perspective view of the core 22 relating to the first modified example.

(With Regard to Magnetic Field Forming Unit)

Figure 15:
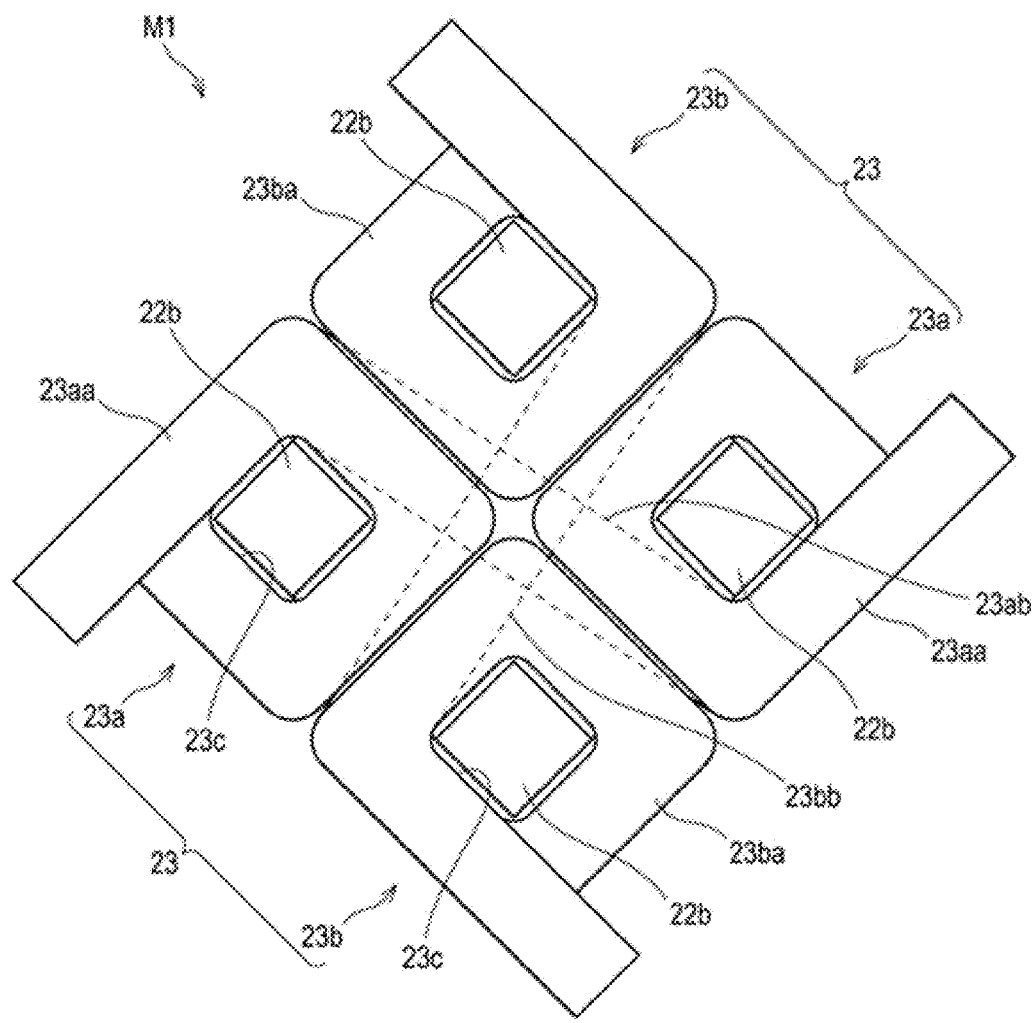
FIG. 15 is a plan view of the magnetic field forming unit relating to the first modified example.
Figure 16:
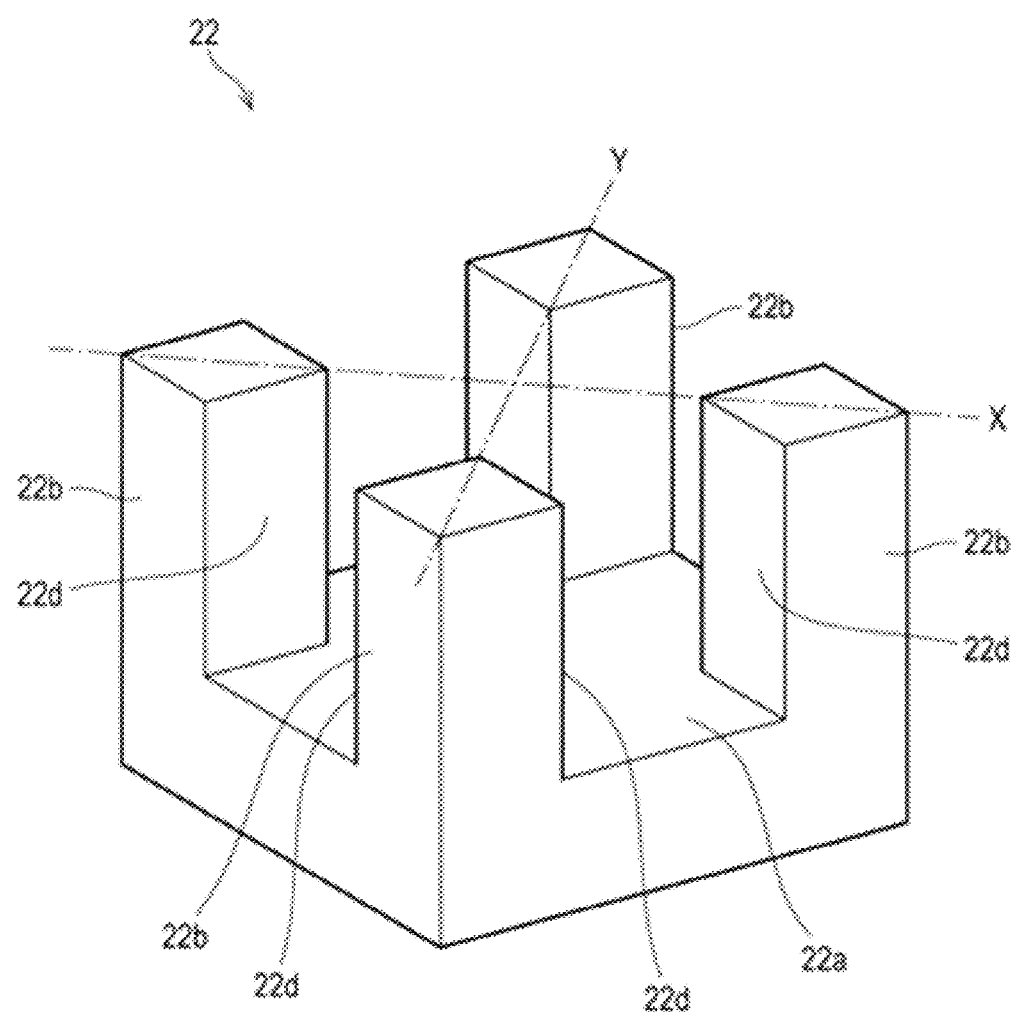
FIG. 16 is an upper-side perspective view of the core relating to the first modified example.

As shown in FIG. 14 and FIG. 15, the magnetic field forming unit M1 is constituted by the core 22 and coils 23 which are wound around portions of the core 22.

(With Regard to Core)

As shown in FIG. 16, for the core 22 relating to this modified example there is provided four pieces of (two pairs of) leg portions 22b around which two pairs of first coil portions 23a and second coil portions 23b, which will be described later, are wound and provided a base unit 22a which connects the leg portions 22b to one another. Each of the two pairs of leg portions 22b is formed to have in a cross-section rectangular shape, and are extending upward from the top surface of the common base unit 22a.

Here, there is used the wording "two pairs of leg portions 22b" from a functional view point that the pairs of the first coil portions 23a and the second coil portions 23b are wound around, but actually, the four pieces of (two pairs of) leg portions 22b relating to the present example have identical shapes respectively and are arranged evenly upward the four corners of the base unit 22a.

The core 22 is formed by a directionless pressed-powder core which is formed by compression-molding a metallic magnetic powder together with a resin by a ferrite magnetic-body and it is a core formed such that the four leg portions 22b which are rod-shaped magnetic-bodies are protruded upward from the four corners of the top surface of the base unit 22a which is a plate-shaped magnetic-body.

As mentioned above, for the reason that two pairs of leg portions 22b are extending from the common base unit 22a, it is possible to form the core 22 in a stable shape when being compared with the core 2 which is constituted by being combined and which relates to the abovementioned exemplified embodiment.

For the core 22 which is formed in this manner, there are formed two magnetic circuits assuming that the pair of leg portions 22b faced in the diagonal direction is a single magnetic circuit, in which portions of the magnetic circuits are shared and the magnetic circuits are orthogonal to each other in the inside thereof.

In particular, the adjacent leg portions 22b within the four pieces of (two pairs of) leg portions 22b have facing surfaces 22d which are extending mutually in parallel and which face each other.

In this manner, for the reason that the adjacent leg portions 22b have the facing surfaces 22d which are extending mutually in parallel and are facing to each other and that the corner portions of the leg portions 22b do not face each other, it becomes possible to use coils of wide widths as the coils 23 which will be arranged between those leg portions. For this reason, it is possible to lower the DC-resistance of the coils 23 and therefore, it is possible to heighten the performance thereof. Further, it become easy for the coils 23, which are respectively wound around the adjacent leg portions 22b, to be arranged closely in contact with each other and it is possible to suppress the magnetic flux leakage and to heighten the magnetic-flux density.

It should be noted that if the facing surfaces 22d are provided for all the leg portions 22b having the adjacent relation such as a configuration relating to the present example, it becomes possible to arrange the all elements in closely contact with each other as a whole and therefore, this configuration is suitable, but the present invention is not limited by such a constitution.

For example, it is allowed to employ a configuration in which only the facing surfaces 22d, which are within the four leg portions 22b and which have normal lines extending in one common direction, are extended mutually in parallel. Even if employing such a constitution, it becomes possible to arrange the elements in closely contact with each other at least for that one direction and therefore, when compared with the cores which do not have the mutually parallel facing surfaces 22d, it is possible to suppress magnetic flux leakage and to heighten the magnetic-flux density.

(With Regard to Coils)

As one example, the coils 23 are Edgewise-coils each of which is formed by an insulation-coated copper wire of a rectangular wire and the coils are constituted by first coil portions 23a which are wound around a pair of leg portions 22b lying at diagonal positions and second coil portions 23b which are wound around another diagonal leg portions 22b. The first coil portions 23a are constituted by two pieces of spiral portion 23aa wound around a pair of leg portions 22b and a coupling portion 23ab which couples the bottom portions of the spiral portions 23aa. The first coil portions 23a are formed in figure-8 shapes seen by the bottom view by two pieces of spiral portions 23aa and a coupling portion 23ab. The two pieces of spiral portions 23aa have winding-wire directions in which the closed-loop directions of the magnetic-paths are same, and they are wound around the pair of leg portions 22b respectively as shown in FIG. 15.

Similarly, the second coil portions 23b are constituted by two pieces of spiral portions 23ba wound around another pair of leg portions 22b and a coupling portion 23bb which couples the bottom portions of the spiral portions 23ba. The second coil portions 23b are formed in figure-8 shapes seen by the bottom view by two pieces of spiral portions 23ba and a coupling portion 23bb. The two pieces of spiral portions 23ba have winding-wire directions in which the closed-loop directions of the magnetic-paths are same, and they are wound around another pair of leg portions 21b respectively as shown in FIG. 15.

In particular, the first coil portions 23a and the second coil portions 23b are respectively formed by winding-wires which are wound in rectangular shapes, in which holes 23c having cross-sectional rectangular shapes are formed at the inner edges thereof, and depending on a configuration that the two pairs of leg portions 22b are passed through the holes 23c respectively, the coils are attached to the two pairs of leg portions 22b.

According to such a constitution, there can be employed a closely contact state between the first coil portions 23a and the second coil portions 23b and also a closely contact state of the first coil portions 23a and the second coil portions 23b with respect to the two pairs of leg portions 22b and therefore, it is possible to suppress the magnetic flux leakage.

Second Modified Example

As shown in FIG. 4, the magnetic field generating-apparatus 1 relating to the abovementioned exemplified embodiment was constituted by including the 2-circuit power supply circuits CP1, CP2 which are provided with the DC-power supplies 4 respectively, but the present invention is not limited by a configuration relating to such a constitution.

Figure 17:
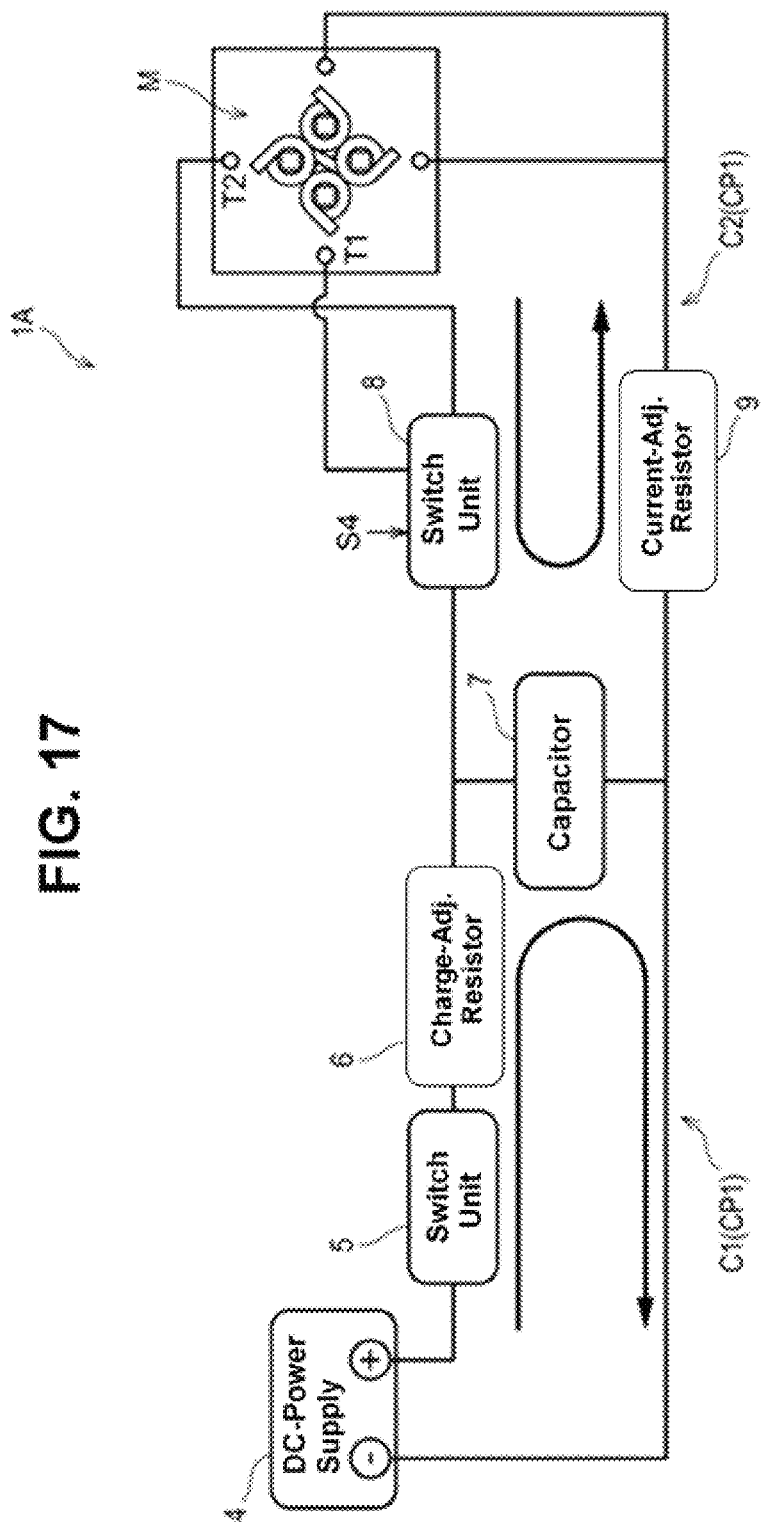
FIG. 17 is an explanatory diagram for explaining a constitution of a magnetic field generating-apparatus relating to a second modified example.
Figure 18:
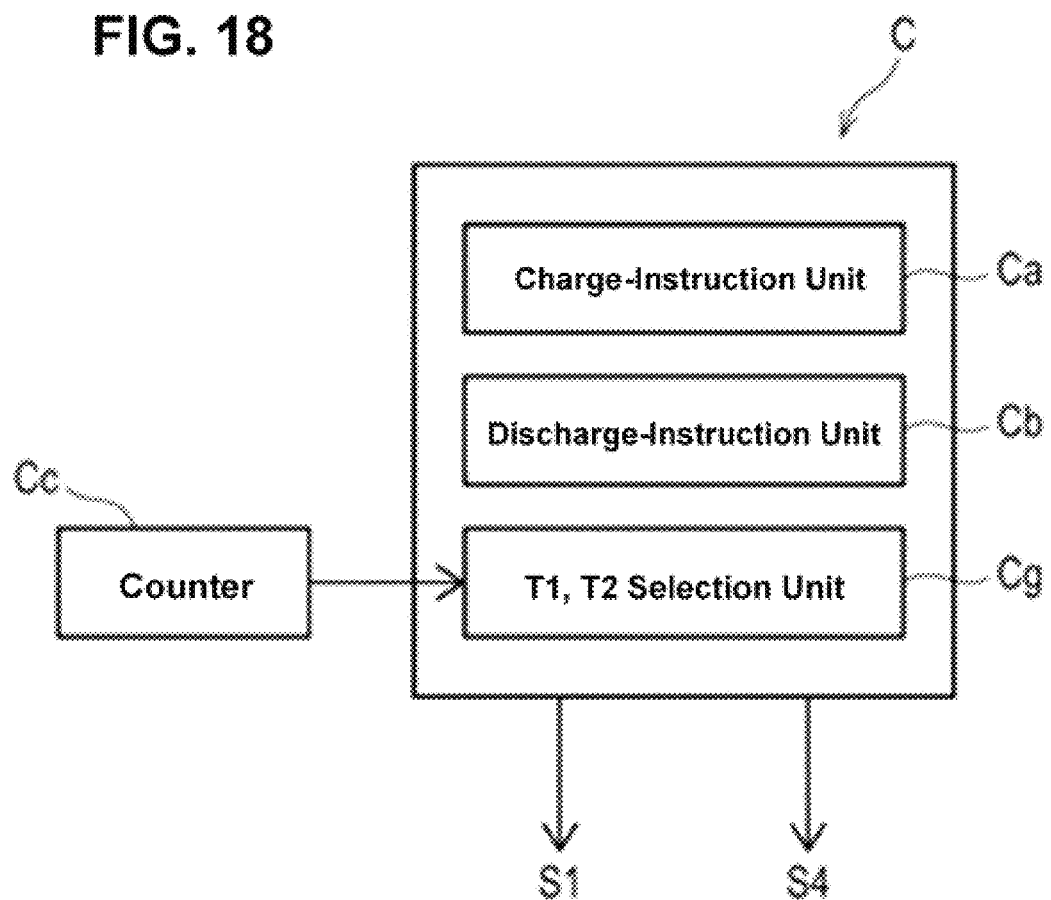
FIG. 18 is a functional diagram of a control unit having a function of selecting terminals, which flow alternating currents, for every pulse.
Figure 19:
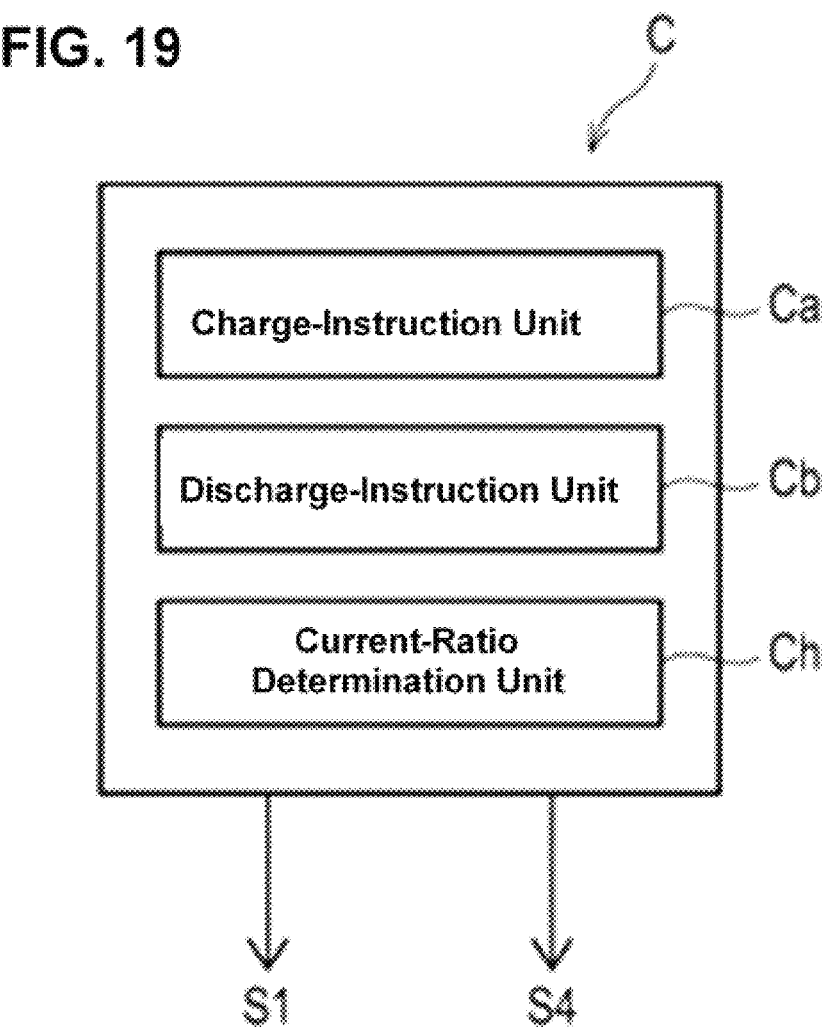
FIG. 19 is a functional diagram of a control unit having a function of determining the ratio of electric currents which are supplied to the first coil portions and the second coil portions.

Next, there will be explained a magnetic field generating-apparatus for biostimulation (magnetic field generating-apparatus 1A) relating to a second modified example mainly with reference to FIG. 17 to FIG. 19. FIG. 17 is an explanatory diagram for explaining a constitution of the magnetic field generating-apparatus 1A relating to the second modified example. FIG. 18 is a functional diagram of a control unit having a function of selecting terminals T1, T2, which flow the alternating currents, for every pulse, and FIG. 19 is a functional diagram of a control unit C having a function of determining the ratio of the electric currents which are supplied to the first coil portions 3a and the second coil portions 3b.

In order to make it possible to supply alternating current to the coils 3, the magnetic field generating-apparatus for biostimulation (magnetic field generating-apparatus 1A) includes: one set of power supply circuit provided with a single DC-power supply 4 (power supply circuit CP1 constituted by a first circuit C1 and a second circuit C2), a control unit C which controls the supply of the alternating currents, and a switch (switch unit 8) for switching the single alternating-current output in the power supply circuit.

By using the switch unit 8, the control unit C switches the target for flowing the alternating current for every one pulse or every few pulses between the first coil portions 3a (Y direction) and the second coil portions 3b (X-direction).

Specifically, the control unit C is provided with a T1, T2 selection unit Cg which has a function of obtaining counted values of a counter Cc counting the pulses of the alternating current and a function of selecting whether to flow the alternating current to the terminal T1 of the first coil portions 3a or whether to flow the alternating current to the terminal T2 of the second coil portions 3b. Depending on the selection of the T2 selection unit Cg, the control unit C transmits a signal S4 with respect to the switch unit 8 so as to flow the alternating current to either one of the terminal T1 of the first coil portions 3a or the terminal T2 of the second coil portions 3b. In this manner, by using time divisional way, the impulse-shaped alternating current generates the magnetic field in the first direction (X-direction) and the magnetic field in the second direction (Y-direction) alternately.

Here, the wording "alternately" means that the timing of the magnetic-field generation is different and this is not limited by the timing in which the magnetic fields are generated at completely different timings, but it is allowed to employ a configuration in which the magnetic fields are generated at the same timing partially for the portions thereof.

In addition, it is allowed for the counter Cc to be a counter which is provided on the outside of the control unit C or on the inside of thereof.

According to such a constitution, for the reason that the target for flowing the electric current is switched for every pulse, it is not necessary to provide a plurality of power supply circuits and the synchronization when applying magnetic fields of different directions becomes easy. Further, by carrying out the controls for the division of the output electric current and for the phase reverse for every one pulse or every few pulses, it is possible to change the application directions of the magnetic field or to continuously apply magnetic fields of plural directions without moving the magnetic field generating-apparatus 1A.

It is preferable that the application interval of the alternating current to each of the abovementioned coil portions 3a, 3b is selected to be shorter than the demagnetization time of each of the coil portions 3a, 3b. If such a constitution is employed, it becomes that the generation timings of the magnetic fields of the respective coil portions 3a, 3b are overlapped and therefore, it is possible to mutually-add (synthesize) the magnetic fields of the respective excited coil portions 3a, 3b.

It should be noted that it is allowed for the control unit C to employ a configuration in which the control of the output electric current is carried out for every determined time period other than to employ a configuration in which the control of the output electric current is carried out for every pulse.

Other than those described above, it is allowed for the control unit C to be provided with a current-ratio determination unit Ch which determines the supplying ratio by which the alternating current generated from one set of electrical circuit (power supply circuit CP1 constituted by the first circuit C1 and the second circuit C2) is supplied with respect to the first coil portions 3a (X-direction) and the second coil portions 3b (Y-direction).

For example, the control unit C transmits the signal S4 with respect to the switch unit 8 such that the electric current is to be applied depending on the ratio determined by the current-ratio determination unit Ch. Then, it is allowed to employ a configuration in which the electric current is applied with respect to the first coil portions 3a (X-direction) and the second coil portions 3b (Y-direction) by the switch unit 8 provided with a transistor (not shown).

In response to the division ratio, it is possible to change the magnetic field generated at that time from 0 degree (X:Y=1:0) to 90 degrees (X:Y=0:1) with respect the X-direction. Further, by inverting either one of the phases and by dividing with an arbitrary ratio, it is possible to change the generated magnetic field from 90 degrees (X:Y=0:1) or more to 180 degrees (X:Y=−1:0) with respect to the X-direction. The magnetic field is "AC" magnetic field and therefore, if the direction can be changed from 0 degree to 180 degrees, it is possible to cover all directions.

Further, similarly as that shown in FIG. 6, it is allowed for the magnetic field generating-apparatus 1A to be further provided with a sensor (muscle electric-potential sensor 10) which detects the electric-potential inside the living body.

For example, the control unit C controls the ratio between the electric current supplied to the first coil portions 3a and the electric current supplied to the second coil portions 3b by a feed-back control depending on the current-ratio determination unit Ch based on the electric-potential detected by the sensor (muscle electric-potential sensor 10).

In this manner, by the fact that the control unit C carries out the feed-back control, it is possible to suitably apply stimulations with respect to a plurality of nerve fibers extending toward every direction by changing the direction.

The abovementioned each exemplified embodiment includes any one of the following technical ideas.

(1) A magnetic field generating-apparatus for biostimulation including:
    a core formed by magnetic material; and
    coils wound around portions of the cores,
    wherein the core includes at least two pairs of leg portions which are juxtaposed each other, in which
    for the respective two pairs of leg portions, there are provided gap-portions which mutually cross each other,
    the coils include first coil portions and second coil portions forming a first magnetic-path and a second magnetic-path between the two pairs of leg portions and the gap-portions respectively; and
    wherein depending on the first coil portions and one pair of leg portions, there is generated a magnetic field of first direction which lies on the first magnetic-path, depending on the second coil portions and the other pair of leg portions, there is generated a magnetic field of second direction which lies on the second magnetic-path, and depending on a magnetic field formed by synthesizing the magnetic field of first direction and the magnetic field of second direction, a living body is stimulated.

(2) The magnetic field generating-apparatus for biostimulation according to the item (1), further including:
    a power supply circuit which supplies alternating current to the coils; and
    a control unit which controls the supply of the alternating current, wherein
    the control unit can control the ratio between the magnitude of the alternating current which is supplied from the power supply circuit to the first coil portions and the magnitude of the electric current which is supplied from the power supply circuit to the second coil portions.

(3) The magnetic field generating-apparatus for biostimulation according to the item (2), further including:
    a sensor which detects the electric-potential inside the living body, wherein
    based on the electric-potential detected by the sensor, the control unit controls the ratio between the electric current supplied to the first coil portions and the electric current supplied to the second coil portions according to feed-back control.

(4) The magnetic field generating-apparatus for biostimulation according to any one of the items (1) to (3), including:

2-circuit power supply circuits which supply alternating currents to the coils; and a control unit which controls the supplies of the alternating currents, wherein the output of one of the power supply circuits is connected to one of the first coil portions and the second coil portions, and the output of the other of the power supply circuits is connected to the other of the first coil portions and the second coil portions.

(5) The magnetic field generating-apparatus for biostimulation according to any one of the items (1) to (4), wherein the voltage applied to the first coil portions and the voltage applied to the second coil portions are different in phase.

(6) The magnetic field generating-apparatus for biostimulation according to the item (5), wherein the absolute value of the difference in phase is less than 180 degrees.

(7) The magnetic field generating-apparatus for biostimulation according to the item (1), further including:

a power supply circuit which supplies alternating current to the coils;

a control unit which controls the supply of the alternating current; and a switch which switches the output of the power supply circuit, wherein the control unit lets the magnetic field of the first direction and the magnetic field of the second direction be generated alternately by switching the target for flowing the alternating current between the first coil portions and the second coil portions caused by the switch for every one pulse or every few pulses.

(8) The magnetic field generating-apparatus for biostimulation according to any one of the items (1) to (7), wherein the core includes connecting portions which connect the leg portions of the respective pairs mutually, the mutual connecting portions for the two pairs of leg portions are arranged at twisted positions, and the end surfaces of the two pairs of leg portions lie on the same plane.

(9) The magnetic field generating-apparatus for biostimulation according to any one of the items (1) to (7), wherein the core includes a base unit which connects the leg portions mutually, and the two pairs of leg portions are extending from the common base unit.

(10) The magnetic field generating-apparatus for biostimulation according to any one of the items (1) to (9), wherein the adjacent leg portions within the two pairs of leg portions include facing surfaces which are extending mutually in parallel and are facing to each other.

(11) The magnetic field generating-apparatus for biostimulation according to any one of the items (1) to (10), wherein the two pairs of leg portions are formed to have rectangular shapes in cross sections; and each of the first coil portion and the second coil portion is formed by a winding-wire wound in a rectangular shape, in which for the inner edge thereof, there is formed a hole having a rectangular shape in cross section, and in which the coil portions are attached to the two pairs of leg portions caused by the configuration that the respective two pairs of leg portions are passed through the holes.

Having described preferred embodiments of the invention with reference to the accompanying drawings, it is to be understood that the invention is not limited to those precise embodiments and that various changes and modifications could be effected therein by one skilled in the art without departing from the spirit or scope of the invention as defined in the appended claims.

What is claimed is:

1. A magnetic field generating apparatus for biostimulation comprising:

a core formed by magnetic material; and coils wound around portions of the core, wherein the core includes at least two pairs of leg portions which are juxtaposed each other, in which for each one of the at least two pairs of leg portions, there are provided gap-portions which mutually cross each other, the coils include first coil portions and second coil portions forming a first magnetic path and a second magnetic path between the at least two pairs of leg portions and the gap-portions respectively; and wherein by the first coil portions and one pair of the at least two pairs of leg portions, there is generated a magnetic field of first direction which lies on the first magnetic path, by the second coil portions and an other pair of the at least two pairs of leg portions, there is generated a magnetic field of second direction which lies on the second magnetic path, and by a magnetic field formed by synthesizing the magnetic field of first direction and the magnetic field of second direction, a living body is configured to be stimulated, and wherein a voltage applied to the first coil portions and a voltage applied to the second coil portions are different in phase, and the absolute value of the difference in phase is less than 180 degrees.

2. The magnetic field generating apparatus for biostimulation according to claim 1, further comprising:

a power supply circuit which supplies alternating current to the coils; and a control unit which controls the supply of the alternating current, wherein the control unit can control the ratio between the magnitude of the alternating current which is supplied from the power supply circuit to the first coil portions and the magnitude of the electric current which is supplied from the power supply circuit to the second coil portions.

3. The magnetic field generating apparatus for biostimulation according to claim 2, further comprising:

a sensor configured to detect an electric potential inside the living body, wherein based on the electric potential detected by the sensor, the control unit controls the ratio between the electric current supplied to the first coil portions and the electric current supplied to the second coil portions according to feed-back control.

4. The magnetic field generating apparatus for biostimulation according to claim 1, comprising:

2-circuit power supply circuits which supply alternating currents to the coils; and a control unit which controls the supplies of the alternating currents, wherein an output of one of the power supply circuits is connected to one of the first coil portions and the second coil portions, and an output of an other of the power supply circuits is connected to the other of the first coil portions and the second coil portions.

5. The magnetic field generating apparatus for biostimulation according to claim 1, further comprising:

a power supply circuit which supplies alternating current to the coils;

a control unit which controls the supply of the alternating current; and a switch which switches an output of the power supply circuit, wherein the control unit controls the magnetic field of the first direction and the magnetic field of the second direction to be generated alternately by switching the alternating current between the first coil portions and the second coil portions within one pulse or a few pulses.

6. The magnetic field generating apparatus for biostimulation according to claim 1, wherein the core includes a first connecting portions which connects the leg portions of the one pair of the at least two pairs of leg portions, and a second connecting portion which connects the leg portions of the other pair of the at least two pairs of leg portions, the first and the second connecting portions for the at least two pairs of leg portions are arranged at crossed positions, and end surfaces of the at least two pairs of leg portions lie on the same plane.

7. The magnetic field generating apparatus for biostimulation according to claim 1, wherein the core includes a common base unit which connects the at least two pairs of leg portions mutually, and the at least two pairs of leg portions are extending from the common base unit.

8. The magnetic field generating apparatus for biostimulation according to claim 1, wherein two neighboring leg portions within the at least two pairs of leg portions include facing surfaces which are extending mutually in parallel and are facing to each other.

9. The magnetic field generating apparatus for biostimulation according to claim 1, wherein the at least two pairs of leg portions are formed to have rectangular shapes in cross sections; and each of the first coil portions and the second coil portions is formed by a winding-wire wound in a rectangular shape, in which for an inner edge thereof, there is formed a hole having a rectangular shape in cross section, and in which the first and the second coil portions are attached to the at least two pairs of leg portions such that respective leg portions of the at least two pairs of leg portions are passed through the holes.

10. A magnetic field generating apparatus for biostimulation comprising:

a core formed by magnetic material; and coils wound around portions of the core, wherein the core includes at least two pairs of leg portions which are juxtaposed each other, in which for each one of the at least two pairs of leg portions, there are provided gap-portions which mutually cross each other, the coils include first coil portions and second coil portions forming a first magnetic path and a second magnetic path between the at least two pairs of leg portions and the gap-portions respectively; and wherein by the first coil portions and one pair of the at least two pairs of leg portions, there is generated a magnetic field of first direction which lies on the first magnetic path, by the second coil portions and an other pair of the at least two pairs of leg portions, there is generated a magnetic field of second direction which lies on the second magnetic path, and by a magnetic field formed by synthesizing the magnetic field of first direction and the magnetic field of second direction, a living body is configured to be stimulated, and wherein the core includes a first connecting portion which connects the leg portions of the one pair of the at least two pairs of leg portions, and a second connecting portion which connects the leg portions of the other pair of the at least two pairs of leg portions, the first and the second connecting portions for the at least two pairs of leg portions are arranged at crossed positions, and end surfaces of the at least two pairs of leg portions lie on the same plane.

11. The magnetic field generating apparatus for biostimulation according to claim 10, further comprising:

a power supply circuit which supplies alternating current to the coils; and a control unit which controls the supply of the alternating current, wherein the control unit can control the ratio between the magnitude of the alternating current which is supplied from the power supply circuit to the first coil portions and the magnitude of the electric current which is supplied from the power supply circuit to the second coil portions.

12. The magnetic field generating apparatus for biostimulation according to claim 11, further comprising:

a sensor configured to detect an electric potential inside the living body, wherein based on the electric potential detected by the sensor, the control unit controls the ratio between the electric current supplied to the first coil portions and the electric current supplied to the second coil portions according to feed-back control.

13. The magnetic field generating apparatus for biostimulation according to claim 10, comprising:

2-circuit power supply circuits which supply alternating currents to the coils; and a control unit which controls the supplies of the alternating currents, wherein an output of one of the power supply circuits is connected to one of the first coil portions and the second coil portions, and an output of an other of the power supply circuits is connected to the other of the first coil portions and the second coil portions.

14. The magnetic field generating apparatus for biostimulation according to claim 10, wherein a voltage applied to the first coil portions and a voltage applied to the second coil portions are different in phase.

15. The magnetic field generating apparatus for biostimulation according to claim 14, wherein an absolute value of the difference in phase is less than 180 degrees.

16. The magnetic field generating apparatus for biostimulation according to claim 10, further comprising:

a power supply circuit which supplies alternating current to the coils;

a control unit which controls the supply of the alternating current; and a switch which switches an output of the power supply circuit, wherein the control unit controls the magnetic field of the first direction and the magnetic field of the second direction to be generated alternately by switching the alternating current between the first coil portions and the second coil portions within one pulse or a few pulses.

17. The magnetic field generating apparatus for biostimulation according to claim 10, wherein the core includes a common base unit which connects the at least two pairs of leg portions mutually, and the at least two pairs of leg portions are extending from the common base unit.

18. The magnetic field generating apparatus for biostimulation according to claim 10, wherein two neighboring leg portions within the at least two pairs of leg portions include facing surfaces which are extending mutually in parallel and are facing to each other.

19. The magnetic field generating apparatus for biostimulation according to claim 10, wherein the at least two pairs of leg portions are formed to have rectangular shapes in cross sections; and each of the first coil portions and the second coil portions is formed by a winding-wire wound in a rectangular shape, in which for an inner edge thereof, there is formed a hole having a rectangular shape in cross section, and in which the first and the second coil portions are attached to the at least two pairs of leg portions such that respective leg portions of the at least two pairs of leg portions are passed through the holes.

\* \* \* \* \*